United States Patent
Shirazi

(10) Patent No.: US 9,290,798 B2
(45) Date of Patent: *Mar. 22, 2016

(54) MANUFACTURING AND PROCESSING POLYMER ARRAYS

(71) Applicant: Affymetrix, Inc., Santa Clara, CA (US)

(72) Inventor: Mohsen Shirazi, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/933,963

(22) Filed: Jul. 2, 2013

(65) Prior Publication Data

US 2014/0018266 A1 Jan. 16, 2014

Related U.S. Application Data

(62) Division of application No. 12/963,593, filed on Dec. 8, 2010, now Pat. No. 8,501,122.

(60) Provisional application No. 61/267,738, filed on Dec. 8, 2009.

(51) Int. Cl.
*C12Q 1/68* (2006.01)
*C12Q 1/00* (2006.01)
*B01L 3/00* (2006.01)
*B01L 9/00* (2006.01)

(52) U.S. Cl.
CPC .............. *C12Q 1/6837* (2013.01); *B01L 3/5085* (2013.01); *B01L 3/50855* (2013.01); *B01J 2219/00317* (2013.01); *B01J 2219/00702* (2013.01); *B01L 9/523* (2013.01); *B01L 2200/0689* (2013.01); *B01L 2200/12* (2013.01); *B01L 2300/0636* (2013.01); *B01L 2300/0829* (2013.01); *B32B 2305/342* (2013.01); *B32B 2457/14* (2013.01); *Y10T 29/49124* (2015.01)

(58) Field of Classification Search
CPC .. C12Q 1/6837; C12Q 1/6834; C12Q 1/6813; C12Q 1/68
USPC ................... 422/553, 552, 551, 547, 500, 50; 506/39, 33
See application file for complete search history.

(56) References Cited

U.S. PATENT DOCUMENTS

| | | | |
|---|---|---|---|
| 4,437,975 A | 3/1984 | Gillespie et al. | |
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 4,988,617 A | 1/1991 | Landegren et al. | |
| 5,143,854 A | 9/1992 | Pirrung et al. | |
| 5,242,794 A | 9/1993 | Whiteley et al. | |
| 5,242,974 A | 9/1993 | Holmes | |
| 5,252,743 A | 10/1993 | Barrett et al. | |
| 5,324,633 A | 6/1994 | Fodor et al. | |
| 5,333,675 A | 8/1994 | Mullis et al. | |
| 5,384,261 A | 1/1995 | Winkler et al. | |
| 5,405,783 A | 4/1995 | Pirrung et al. | |
| 5,409,818 A | 4/1995 | Davey et al. | |
| 5,412,087 A | 5/1995 | McGall et al. | |
| 5,413,909 A | 5/1995 | Bassam et al. | |
| 5,424,186 A | 6/1995 | Fodor et al. | |
| 5,451,683 A | 9/1995 | Barrett et al. | |
| 5,482,867 A | 1/1996 | Barrett et al. | |
| 5,491,074 A | 2/1996 | Aldwin et al. | |
| 5,494,810 A | 2/1996 | Barany et al. | |
| 5,527,681 A | 6/1996 | Holmes | |
| 5,541,061 A | 7/1996 | Fodor et al. | |
| 5,550,215 A | 8/1996 | Holmes | |
| 5,554,517 A | 9/1996 | Davey et al. | |
| 5,571,639 A | 11/1996 | Hubbell et al. | |
| 5,578,832 A | 11/1996 | Trulson et al. | |
| 5,593,839 A | 1/1997 | Hubbell et al. | |
| 5,599,695 A | 2/1997 | Pease et al. | |
| 5,624,711 A | 4/1997 | Sundberg et al. | |
| 5,631,734 A | 5/1997 | Stern et al. | |
| 5,733,729 A | 3/1998 | Lipshutz et al. | |
| 5,744,305 A | 4/1998 | Fodor et al. | |
| 5,795,716 A | 8/1998 | Chee | |
| 5,800,992 A | 9/1998 | Fodor et al. | |
| 5,831,070 A | 11/1998 | Pease et al. | |
| 5,834,758 A | 11/1998 | Trulson et al. | |
| 5,837,832 A | 11/1998 | Chee et al. | |
| 5,856,092 A | 1/1999 | Dale et al. | |
| 5,856,101 A | 1/1999 | Hubbell et al. | |
| 5,858,659 A | 1/1999 | Sapolsky et al. | |
| 5,861,245 A | 1/1999 | McClelland et al. | |
| 5,871,928 A | 2/1999 | Fodor et al. | |
| 5,874,219 A | 2/1999 | Rava et al. | |
| 5,889,165 A | 3/1999 | Fodor et al. | |
| 5,902,723 A | 5/1999 | Dower et al. | |
| 5,936,324 A | 8/1999 | Montagu | |
| 5,959,098 A | 9/1999 | Goldberg et al. | |
| 5,968,740 A | 10/1999 | Fodor et al. | |
| 5,974,164 A | 10/1999 | Chee | |
| 5,981,185 A | 11/1999 | Matson et al. | |
| 5,981,956 A | 11/1999 | Stern | |

(Continued)

FOREIGN PATENT DOCUMENTS

| | | | | |
|---|---|---|---|---|
| EP | 1 652 580 | * | 5/2006 | ............... B01J 19/00 |
| WO | 8810315 A1 | | 12/1988 | |

(Continued)

OTHER PUBLICATIONS

Merriam-Webster.com definition of 'border', obtained on May 5, 2015, p. 1-4.*

*Primary Examiner* — Christine T Mui

(74) *Attorney, Agent, or Firm* — Banner & Witcoff, Ltd.

(57) ABSTRACT

The invention provides methods to process multiple microarrays by providing a microarray plate and processing plates. In an embodiment of the invention, methods for assembling microarray plates by using wafers are described for high throughput microarray processing.

16 Claims, 17 Drawing Sheets

(56) References Cited

U.S. PATENT DOCUMENTS

| | | | |
|---|---|---|---|
| 6,013,449 A | 1/2000 | Hacia et al. |
| 6,020,135 A | 2/2000 | Levine et al. |
| 6,025,601 A | 2/2000 | Trulson et al. |
| 6,033,860 A | 3/2000 | Lockhart et al. |
| 6,040,138 A | 3/2000 | Lockhart et al. |
| 6,040,193 A | 3/2000 | Winkler et al. |
| 6,045,996 A | 4/2000 | Cronin et al. |
| 6,063,603 A | 5/2000 | Davey et al. |
| 6,066,454 A | 5/2000 | Lipshutz et al. |
| 6,090,555 A | 7/2000 | Fiekowsky et al. |
| 6,136,269 A | 10/2000 | Winkler et al. |
| 6,141,096 A | 10/2000 | Stern et al. |
| 6,147,205 A | 11/2000 | McGall et al. |
| 6,177,248 B1 | 1/2001 | Oliner et al. |
| 6,185,030 B1 | 2/2001 | Overbeck |
| 6,185,561 B1 | 2/2001 | Balaban et al. |
| 6,188,783 B1 | 2/2001 | Balaban et al. |
| 6,197,506 B1 | 3/2001 | Fodor et al. |
| 6,201,639 B1 | 3/2001 | Overbeck |
| 6,218,803 B1 | 4/2001 | Montagu et al. |
| 6,223,127 B1 | 4/2001 | Berno |
| 6,225,625 B1 | 5/2001 | Pirrung et al. |
| 6,229,911 B1 | 5/2001 | Balaban et al. |
| 6,269,846 B1 | 8/2001 | Overbeck et al. |
| 6,284,460 B1 | 9/2001 | Fodor et al. |
| 6,300,063 B1 | 10/2001 | Lipshutz et al. |
| 6,300,070 B1 | 10/2001 | Boles et al. |
| 6,300,675 B1 | 10/2001 | Tamai |
| 6,308,170 B1 | 10/2001 | Balaban |
| 6,309,822 B1 | 10/2001 | Fodor et al. |
| 6,333,179 B1 | 12/2001 | Matsuzaki et al. |
| 6,361,947 B1 | 3/2002 | Dong et al. |
| 6,368,799 B1 | 4/2002 | Chee |
| 6,386,749 B1 | 5/2002 | Watts et al. |
| 6,391,592 B1 | 5/2002 | Su et al. |
| 6,391,623 B1 | 5/2002 | Besemer et al. |
| 6,410,276 B1 | 6/2002 | Burg et al. |
| 6,428,752 B1 | 8/2002 | Montagu |
| 6,582,908 B2 | 6/2003 | Fodor et al. |
| 6,582,938 B1 | 6/2003 | Su et al. |
| 6,632,611 B2 | 10/2003 | Su et al. |
| 6,858,412 B2 | 2/2005 | Willis et al. |
| 6,872,529 B2 | 3/2005 | Su |
| 6,958,225 B2 | 10/2005 | Dong |
| 7,689,022 B2 | 3/2010 | Weiner et al. |
| 8,652,774 B2 | 2/2014 | Yamamoto et al. |
| 2002/0183936 A1 | 12/2002 | Kulp et al. |
| 2003/0097222 A1 | 5/2003 | Craford et al. |
| 2003/0120432 A1 | 6/2003 | Zhou et al. |
| 2003/0124599 A1* | 7/2003 | Chen .................. B01J 19/0046 506/39 |
| 2003/0157700 A1* | 8/2003 | Spence ............... B01J 19/0046 506/13 |
| 2004/0002818 A1 | 1/2004 | Kulp et al. |
| 2004/0012676 A1 | 1/2004 | Weiner et al. |
| 2004/0049354 A1 | 3/2004 | Loraine et al. |
| 2004/0126840 A1 | 7/2004 | Cheng et al. |
| 2005/0026299 A1* | 2/2005 | Bhattacharjee et al. ...... 436/169 |
| 2006/0088863 A1 | 4/2006 | Yamamoto et al. |
| 2007/0148599 A1 | 6/2007 | True |
| 2008/0038559 A1 | 2/2008 | True |

FOREIGN PATENT DOCUMENTS

| | | | |
|---|---|---|---|
| WO | 9611878 A1 | 4/1996 |
| WO | 9906995 A1 | 2/1999 |
| WO | 9936760 A1 | 7/1999 |
| WO | 9947964 A1 | 9/1999 |
| WO | 0058516 A2 | 10/2000 |
| WO | 0158593 A1 | 8/2001 |
| WO | 2007081410 A2 | 7/2007 |

\* cited by examiner

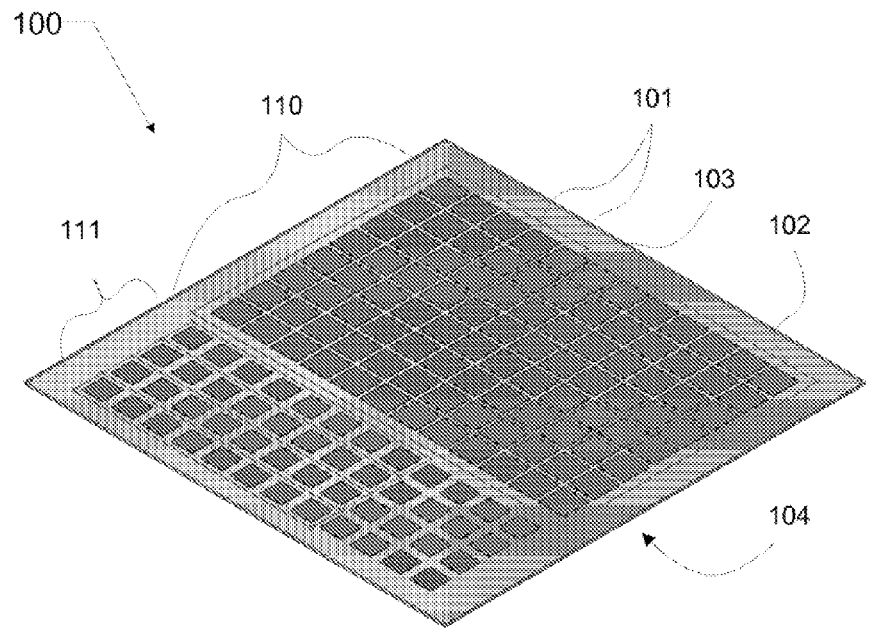
Fig. 1A
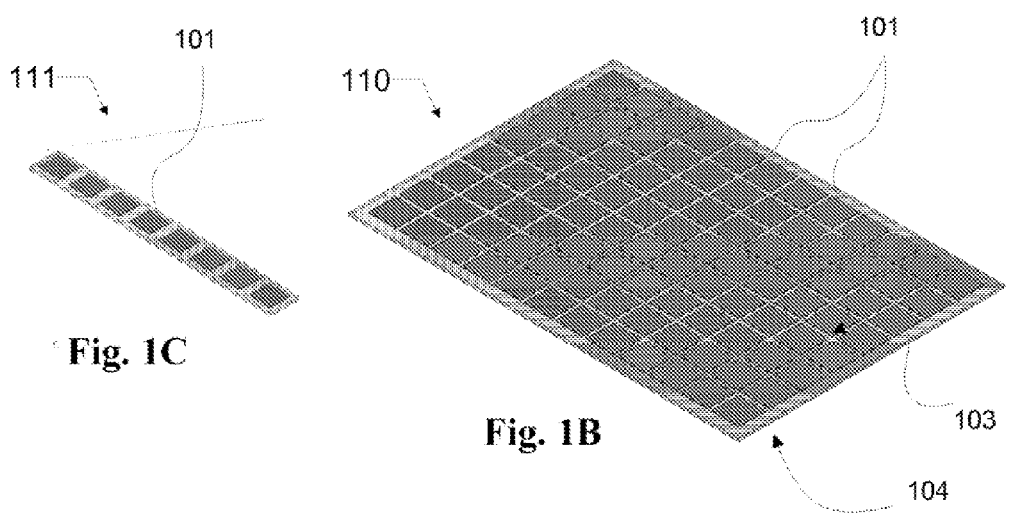
Fig. 1C
Fig. 1B

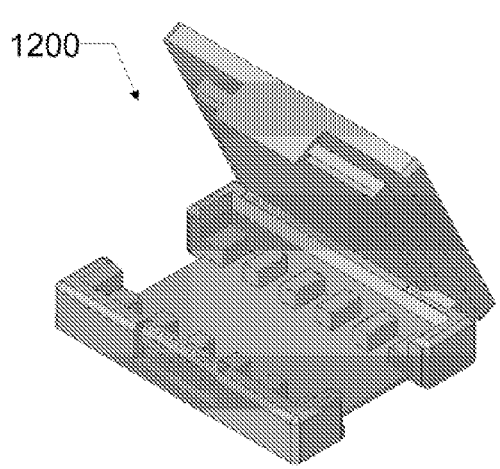 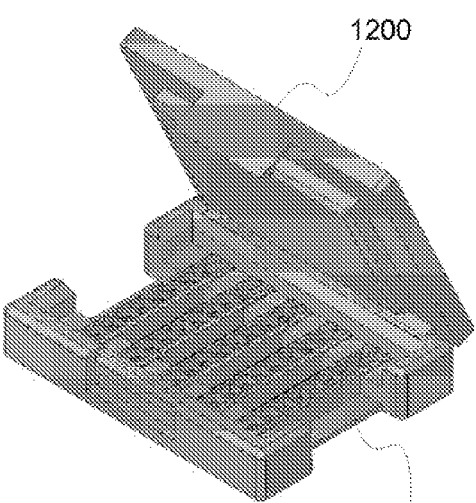
Fig. 13A  Fig. 13B
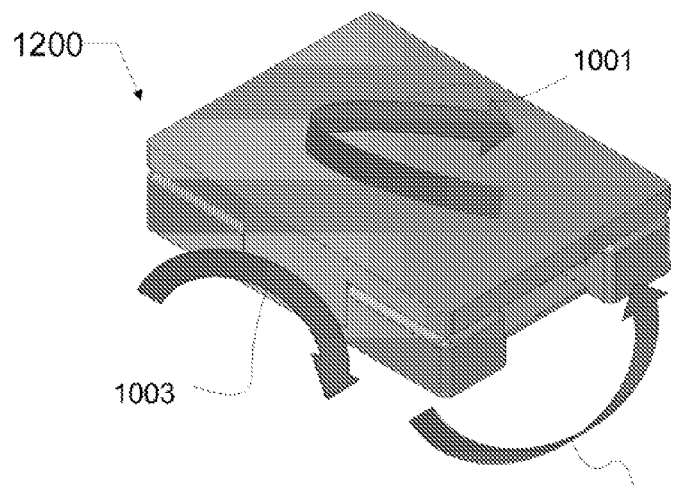
Fig. 13C

MANUFACTURING AND PROCESSING POLYMER ARRAYS

RELATED APPLICATIONS

This application is a divisional of U.S. application Ser. No. 12/963,593, filed Dec. 8, 2010, now U.S. Pat. No. 8,501,122, which claims priority to U.S. Provisional Application No. 61/267,738, filed Dec. 8, 2009, both of which are herein incorporated by reference in their entirety for all purposes.

FIELD OF INVENTION

The invention resides in the field of sensors, such as microarrays, for analyzing samples, and more particularly modular arrays of such sensors for simultaneous processing and analyses of multiple sensors. In accordance with one aspect of the invention, methods for constructing a microarray plate and a microarray strip plate are provided for the fabrication of high density polymer arrays and assortments of high density arrays.

BACKGROUND OF THE INVENTION

Probe arrays, particularly microarrays, such as GENE-CHIP® arrays from Affymetrix, have wide ranging applications in the pharmaceutical, biotechnology and medical industries. In general, a probe array is exposed to a sample, such that probes bind to analytes or targets (if any) in the sample to which the probes have affinity. The probe arrays are then scanned to determine to which probes the target(s) in the sample have hybridized. The identity of the probes hybridized to the sample provides various information regarding the target(s) in the sample. For example, arrays are useful for sequencing target nucleic acids, expression monitoring, detecting mutations in targets, estimating copy number of targets or simply detecting the presence of a target (e.g., of a particular pathogen).

The field of nucleic acid assays has been transformed by microarrays which allow monitoring of gene expression events, expression profiling, diagnostic and genotyping analyses, among other applications. Substrates bearing arrays of probes (fragments of nucleic acids) are preferably produced or manufactured in a manner that allows assays such as expression monitoring, genotyping and other studies to be performed accurately, reproducibly and efficiently. With more sensitive applications being contemplated for microarrays in the fields of pharmacogenomics and diagnostics, for example, there exists a need in the art for additional devices for manufacturing and processing of microarrays.

SUMMARY OF THE INVENTION

According to one aspect of the invention, a method is provided for assembling a sensor plate by attaching a substrate with a plurality of sensors to a support plate. The substrate is aligned to the support plate with a pre-determined alignment. The support is fixedly attached to the support plate in the pre-determined alignment forming the sensor plate. The support plate includes structural elements to support the surrounding border of each sensor from the inactive side of the substrate. The structural elements maintain the structure of each sensor such that the sensors can be scanned. The substrate protrudes from the base of the support plate sufficiently to facilitate dipping the substrate into a reservoir of a processing plate.

According to a further embodiment, a method is provided for assembling a microarray plate by attaching a wafer section to the support plate. The support plate has structural elements such as walls or ridges to maintain the flatness of each microarray by supporting the inactive side of each microarray in the assembled microarray plate. The wafer section is placed and aligned on top of the support plate by using at least one wafer alignment feature on the support plate. The wafer section is directly attached to the top side of the support plate such that the plurality of structural elements supports the inactive side of each microarray on the wafer section to produce a microarray plate. The wafer section can be bonded using a curable adhesive. The support plate includes at least one support plate alignment feature to align the support plate to a processing plate, which is used to process the plurality of microarrays on the wafer.

In another aspect of the invention, a method is provided for assembling a moduled microarray by assembling a plurality of sensor plates to a frame. The plurality of sensor plates are attached to the frame by engaging at least one attachment feature on the support plate to the corresponding attachment features on the frame and/or the support plate of an adjacent sensor plate so as to guide the sensor plate into the pre-determined alignment with the support to produce an array of sensors. In a further aspect, a method is provided for assembling a moduled microarray plate by assembling a plurality of microarray strip plates.

BRIEF DESCRIPTION OF THE DRAWINGS

The accompanying drawings, which are incorporated in and form a part of this specification, illustrate embodiments of the invention and, together with the description, serve to explain various aspects of the invention:

FIGS. 1A, 1B, and 1C depict an example of a wafer and how it can be diced into wafer sections and wafer strips. FIG. 1A shows an undiced wafer. FIG. 1B illustrates a wafer section of 8×12 microarrays. FIG. 1C illustrates a wafer strip of 1×8 microarrays.

FIG. 2A depicts a support plate. FIG. 2B shows a fully assembled microarray plate.

FIG. 4A shows a wafer strip. FIG. 4B shows a strip support. FIG. 4C shows an assembled microarray strip plate.

FIG. 5A shows a microarray strip plate being assembled onto a frame. FIG. 5B shows a microarray strip plate that has been assembled onto a frame. FIG. 5C depicts a moduled microarray plate comprising of a plurality of microarray strip plates assembled into a frame.

FIG. 6A shows a microarray plate being assembled onto a hybridization tray. FIG. 6B shows an assembled microarray plate with a hybridization tray.

FIG. 8A shows another example of a microarray plate. FIG. 8B shows the microarray plate being assembled onto a hybridization plate. FIG. 8C shows an assembled microarray plate with a hybridization plate.

FIG. 11A shows a microarray strip plate being assembled onto a hybridization strip plate. FIG. 11B shows examples of the various directions that an assembled microarray strip plate with a hybridization strip plate can be rotated.

FIG. 12A shows an opened clamping device. FIG. 12B shows an assembled microarray plate with a hybridization plate in a clamping device. FIG. 12C shows examples of the various directions that an assembled microarray plate with a hybridization plate can be rotated.

FIGS. 13A, 13B, and 13C depict another example of a clamping device. FIG. 13A shows an opened empty clamping device. FIG. 13B illustrates a plurality of assembled microarray strip plates with hybridization strip plates in a clamping device. FIG. 13C shows the various directions that the assembled microarray strip plates with hybridization strip plates can be rotated.

FIG. 14A shows a microarray plate being assembled onto a stain plate. FIG. 14B shows an assembled microarray plate with a stain plate.

FIG. 15A shows a microarray strip plate being assembled onto a stain strip plate. FIG. 15B shows an assembled microarray strip plate with a stain strip plate.

FIG. 16A shows a microarray plate being assembled onto a detection plate. FIG. 16B shows an assembled microarray plate with a detection plate.

FIG. 17A shows a microarray strip plate being assembled onto a scan strip plate. FIG. 17B shows an assembled microarray strip plate with a scan strip plate.

DETAILED DESCRIPTION OF THE INVENTION

Figure 2A:
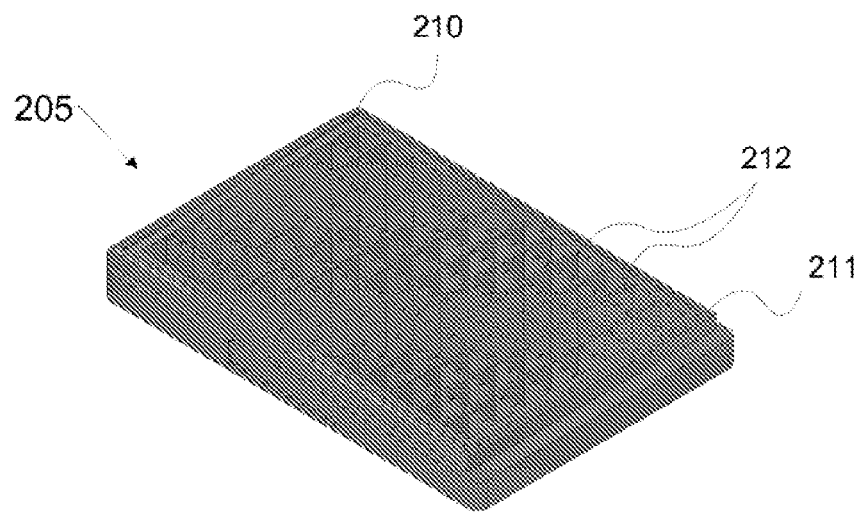
FIGS. 2A and 2B depict parts of an exemplary microarray plate.

Although the invention will be described in conjunction with the exemplary embodiments, the invention is not limited these embodiments. On the contrary, the invention encompasses alternatives, modifications and equivalents, which may be included within the spirit and scope of the invention. The invention has many embodiments and relies on many patents, applications and other references for details known to those of the art. Therefore, when a patent, application, or other reference is cited or repeated below, the entire disclosure of the document cited is incorporated by reference in its entirety for all purposes as well as for the proposition that is recited. All documents, e.g., publications and patent applications, cited in this disclosure, including the foregoing, are incorporated herein by reference in their entireties for all purposes to the same extent as if each of the individual documents were specifically and individually indicated to be so incorporated herein by reference in its entirety.

As used in this application, the singular form "a," "an," and "the" include plural references unless the context clearly dictates otherwise. The term "an agent," for example, includes a plurality of agents, including mixtures thereof.

Throughout this disclosure, various aspects of this invention can be presented in a range format. When a description is provided in range format, this is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

The practice of the invention may employ, unless otherwise indicated, conventional techniques and descriptions of organic chemistry, polymer technology, molecular biology (including recombinant techniques), cell biology, biochemistry, and immunology, which are within the skill of one of skill in the art. Such conventional techniques include polymer array synthesis, hybridization, ligation, and detection of hybridization using a detectable label. Specific illustrations of suitable techniques are provided by reference to the examples herein below. However, other equivalent conventional procedures may also be employed. Such conventional techniques and descriptions may be found in standard laboratory manuals, such as *Genome Analysis: A Laboratory Manual Series (Vols. I-IV)*, *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), Stryer, L. (1995), *Biochemistry*, 4th Ed., Freeman, N.Y., Gait, *Oligonucleotide Synthesis: A Practical Approach*, (1984), IRL Press, London, Nelson and Cox (2000), Lehninger, *Principles of Biochemistry*, $3^{rd}$ Ed., W. H. Freeman Pub., New York, N.Y., and Berg et al. (2002), *Biochemistry*, $5^{th}$ Ed., W. H. Freeman Pub., New York, N.Y., all of which are herein incorporated in their entirety by reference for all purposes.

The invention may employ arrays of probes on solid substrates in some embodiments. Methods and techniques applicable to polymer (including nucleic acid and protein) array synthesis have been described in WO Application Serial No. 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, and in WO 99/36760 and WO 01/58593, which are all incorporated herein by reference in their entirety for all purposes. Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the invention include, but are not limited to, those that are commercially available from Affymetrix (Santa Clara, Calif.) under the brand name GENECHIP®. Example arrays are shown on the website at affymetrix.com.

Probe arrays have many uses including, but are not limited to, gene expression monitoring, profiling, library screening, genotyping and diagnostics. Methods of gene expression monitoring and profiling are described in U.S. Pat. Nos. 5,800,992, 6,013,449, 6,020,135, 6,033,860, 6,040,138, 6,177,248 and 6,309,822. Genotyping methods, and uses thereof, are disclosed in U.S. patent application Ser. No. 10/442,021 (abandoned) and U.S. Pat. Nos. 5,856,092, 6,300, 063, 5,858,659, 6,284,460, 6,361,947, 6,368,799, 6,333,179, and 6,872,529. Other uses are described in U.S. Pat. Nos. 5,871,928, 5,902,723, 6,045,996, 5,541,061, and 6,197,506.

Samples can be process by various methods before analysis. Prior to, or concurrent with, analysis, a nucleic acid sample may be amplified by a variety of mechanisms, some of which may employ PCR. (S e, for example, *PCR Technology: Principles and Applications for DNA Amplification*, Ed. H. A. Erlich, Freeman Press, NY, N.Y., 1992; PCR Protocols: A Guide to Methods and Applications, Eds. Innis, et al., Academic Press, San Diego, Calif., 1990; Mattila et al., *Nucleic Acids Res.*, 19:4967, 1991; Eckert et al., *PCR Methods and Applications*, 1:17, 1991; PCR, Eds. McPherson et al., IRL Press, Oxford, 1991; and U.S. Pat. Nos. 4,683,202, 4,683, 195, 4,800,159 4,965,188, and 5,333,675, each of which is incorporated herein by reference in their entireties for all purposes. The sample may also be amplified on the array. (See, for example, U.S. Pat. No. 6,300,070 and U.S. patent application Ser. No. 09/513,300 (abandoned), all of which are incorporated herein by reference).

Other suitable amplification methods include the ligase chain reaction (LCR) (see, for example, Wu and Wallace, *Genomics*, 4:560 (1989), Landegren et al., *Science*, 241:1077 (1988) and Barringer et al., *Gene*, 89:117 (1990)), transcription amplification (Kwoh et al., *Proc. Natl. Acad. Sci. USA*, 86:1173 (1989) and WO 88/10315), self sustained sequence replication (Guatelli et al., *Proc. Nat. Acad. Sci. USA*, 87:1874 (1990) and WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245) and nucleic acid based sequence amplification (NABSA). (See also, U.S. Pat. Nos. 5,409,818, 5,554, 517, and 6,063,603, each of which is incorporated herein by reference). Other amplification methods that may be used are described in, for instance, U.S. Pat. Nos. 6,582,938, 5,242, 794, 5,494,810, and 4,988,617, each of which is incorporated herein by reference.

Additional methods of sample preparation and techniques for reducing the complexity of a nucleic sample are described in Dong et al., *Genome Research*, 11:1418 (2001), U.S. Pat. Nos. 6,361,947, 6,391,592, 6,632,611, 6,872,529 and 6,958, 225, and in U.S. patent application Ser. No. 09/916,135 (abandoned).

Hybridization assay procedures and conditions will vary depending on the application and are selected in accordance with known general binding methods, including those referred to in Maniatis et al., *Molecular Cloning: A Laboratory Manual*, $2^{nd}$ Ed., Cold Spring Harbor, N.Y., (1989); Berger and Kimmel, *Methods in Enzymology, Guide to Molecular Cloning Techniques*, Vol. 152, Academic Press, Inc., San Diego, Calif. (1987); Young and Davism, *Proc. Nat'l. Acad. Sci.*, 80:1194 (1983). Methods and apparatus for performing repeated and controlled hybridization reactions have been described in, for example, U.S. Pat. Nos. 5,871, 928, 5,874,219, 6,045,996, 6,386,749, and 6,391,623 each of which are incorporated herein by reference.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than about 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations or conditions of 100 mM MES, 1 M [Na+], 20 mM EDTA, 0.01% Tween-20 and a temperature of 30-50° C., or at about 45-50° C. Hybridizations may be performed in the presence of agents such as herring sperm DNA at about 0.1 mg/ml, acetylated BSA at about 0.5 mg/ml. As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GENECHIP® Mapping Assay Manual, 2004.

Hybridization signals can be detected by conventional methods, such as described by, e.g., U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625, U.S. patent application Ser. No. 10/389,194 (U.S. Patent Application Publication No. 2004/0012676, allowed on Nov. 9, 2009) and PCT Application PCT/US99/06097 (published as WO 99/47964), each of which is hereby incorporated by reference in its entirety for all purposes).

The practice of the invention may also employ conventional biology methods, software and systems. Computer software products of the invention typically include, for instance, computer readable medium having computer-executable instructions for performing the logic steps of the method of the invention. Suitable computer readable medium include, but are not limited to, a floppy disk, CD-ROM/DVD/ DVD-ROM, hard-disk drive, flash memory, ROM/RAM, magnetic tapes, etc. The computer executable instructions may be written in a suitable computer language or combination of several computer languages. Basic computational biology methods which may be employed in the invention are described in, for example, Setubal and Meidanis et al., *Introduction to Computational Biology Methods*, PWS Publishing Company, Boston, (1997); Salzberg, Searles, Kasif, (Ed.), *Computational Methods in Molecular Biology*, Elsevier, Amsterdam, (1998); Rashidi and Buehler, *Bioinformatics Basics: Application in Biological Science and Medicine*, CRC Press, London, (2000); and Ouelette and Bzevanis *Bioinformatics: A Practical Guide for Analysis of Gene and Proteins*, Wiley & Sons, Inc., $2^{nd}$ ed., (2001). (See also, U.S. Pat. No. 6,420,108).

The invention can make use of various computer program products and software for a variety of purposes, such as probe design, management of data, analysis, and instrument operation. (See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170).

Genetic information obtained from analysis of sensors can be transferred over networks such as the internet, as disclosed in, for instance, U.S. Patent Application Publication No. 20030097222, U.S. Patent Application Publication No. 20020183936, abandoned, (U.S. Patent Application Publication No. 20030100995, abandoned, U.S. Patent Application Publication No. 20030120432, abandoned, U.S. Patent Application Publication No. 20040002818, abandoned, U.S. Patent Application Publication No. 20040126840, abandoned, U.S. Patent Application Publication No. 20040049354, abandoned, and 60/482,389 (expired).

U.S. patent application Ser. No. 11/243,621, filed Oct. 4, 2005, Ser. No. 10/456,370, filed on Jun. 6, 2003 (now abandoned), and 61/267,738, filed on Dec. 8, 2009 describe different aspects of constructing sensor plates, sensor strip plates, processing plates or high-throughput (HT) plates, which may be useful in conjunction with the invention. Each of these applications is hereby incorporated by reference herein in their entirety for all purposes.

I. DEFINITIONS

The application refers to array of sensor, arrays of probes and arrays of microarrays. A probe array is a plurality of probes attached to a surface of a substrate. Usually each different type of probe occupies a different area of the support and it is known or determinable, which of the different probes occupy different areas. There are usually multiple copies of the same probe within any one of the different areas. Probe arrays can be prepared by in situ synthesis on the substrate or by spotting of probes. Probe arrays can also be formed by distributing microparticles bearing probes to discrete locations (e.g., indentations) of a support. A microarray is a small array (e.g., no more than 5, 2 or 1 cm$^2$) often characterized by a large number (e.g., at least $10^2$, $10^3$, $10^4$, $10^5$ or $10^6$) of probes and/or high density of different probes (e.g., $10^2$-$10^7$ per cm$^2$). The types of molecules in the probe array can be identical or different from each other. The probe array can assume a variety of formats, including, but not limited to, libraries of soluble molecules, and libraries of compounds tethered to resin beads, silica chips, or other solid supports. A probe array may include polymers of a given length having all possible monomer sequences made up of a specific set of monomers, or a specific subset of such a probe array. In other cases a probe array may be formed from inorganic materials (see Schultz et al., PCT application WO 96/11878).

The term "array of sensors" refers to a systematic arrangement of sensors amenable to simultaneous analysis, usually in rows and columns. The sensors can be probe arrays, such as microarrays, or any types of sensor or probes described herein. An exemplary sensor array is a 12 sensor by 8 sensor array of microarrays, optionally with the individually microarrays being spaced as for the wells on a 96-well microtiter plate. Examples of an array of sensors include, for example, a sensor plate, sensor strip, a microarray plate, a microarray strip. An array of sensors may include any number of sensors, and if the sensors are probe arrays, the probe arrays can include any number of probes.

The term "detection plate" or "detection tray" as used herein refers to a body having at least one well and at least one optically transparent window. A detection plate is a device used during the identification of the hybridization events on a plurality of sensors, such as from a sensor plate. Taking a sensor plate as an example, the corresponding detection plate is designed to receive the sensor plate. In one embodiment, the wells are filled with a solution such that the sensors from the sensor plate are submerged when the sensor plate and the detection plates are assembled. The scanning of the sensors is performed through the optically transparent window which can be made from a low-fluorescence material such as fused silica, Zeonor (Nionex), etc. Optionally, a detection plate can have a physical barrier resistant to the passage of liquids around the individual wells or around a plurality of wells.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization" as used herein refers to the process in which two single-stranded polynucleotides bind noncovalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than about 1 M and a temperature of at least 25° C. For example, conditions of 5×SSPE (750 mM NaC, 50 mM NaPhosphate, 5 mM EDTA, pH 7.4) and a temperature of 25-30° C. are suitable for allele-specific probe hybridizations or conditions of 100 mM MES, 1 M [Na+], 20 mM EDTA, 0.01% Tween-20 and a temperature of 30-50° C., preferably at about 45-50° C. Hybridizations may be performed in the presence of agents such as herring sperm DNA at about 0.1 mg/ml, acetylated BSA at about 0.5 mg/ml. As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GENECHIP® Mapping Assay Manual, 2004.

The term "monomer" as used herein refers to any member of the set of molecules that can be joined together to form an oligomer or polymer. The set of monomers useful in the invention includes nucleotides and nucleosides for nucleic acid synthesis and the set of L-amino acids, D-amino acids, or synthetic amino acids for polypeptide synthesis. Different basis sets of monomers may be used at successive steps in the synthesis of a polymer.

The term "mRNA" or "mRNA transcripts" as used herein, includes, but is not limited to, pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate.

The term "nucleic acid" as used herein refers to a polymeric form of nucleotides of any length, either ribonucleotides, deoxyribonucleotides or peptide nucleic acids (PNAs) or (Locked nucleic acids, LNAs), that include purine and pyrimidine bases, or other natural, chemically or biochemically modified, non-natural, or derivatized nucleotide bases. Nucleic acids can be single or double stranded. The backbone of the nucleic acid can include sugars and phosphate groups, as may typically be found in RNA or DNA, or modified or substituted sugar or phosphate groups. A nucleic acid may include modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

Nucleic acids can be isolated from natural sources, recombinantly produced or artificially synthesized and mimetics thereof, such as LNA, "Locked nucleic acid". A further example of a nucleic acid is a peptide nucleic acid (PNA). Double stranded nucleic acid usually pair by Watson-Crick pairing but can also pair by Hoogsteen base pairing which has been identified in certain tRNA molecules and postulated to exist in a triple helix. The term "oligonucleotide" refers to a nucleic acid of about 7-100 bases, (e.g., 10-50 or 15-25).

A probe has specific affinity for a target (or analyte) in a sample. For nucleic acid probes and nucleic acid targets, specific affinity is primarily determined by ability to form Watson Crick complementary base pairs on hybridization. For example, an oligonucleotide probe can be designed to be perfectly complementary to its intended target. Targets may be naturally-occurring or man-made molecules. Also, they can be employed in their unaltered state or as aggregates with other species. Targets may be attached, covalently or noncovalently, to a binding member, either directly or via a specific binding substance. Examples of targets include antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. U.S. Pat. No. 6,582,908 provides an example of arrays having all possible combinations of nucleic acid-based probes having a length of 10 bases, and 12 bases or more. Nucleic acid probes can be, for example, oligonucleotides or cDNAs. Probes can be linear. A probe may also consist of an open circle molecule, comprising a nucleic acid having left and right arms whose sequences are complementary to the target, and separated by a linker region. (see, e.g., U.S. Pat. No. 6,858,412, and Hardenbol et al., *Nat. Biotechnol.*, 21(6):673 (2003). A probe, such as a nucleic acid, can be attached directly to a microparticle, and the microparticle attached to the support, for example in an indentation or divot in the support. Examples of encoded microparticles, methods of making the same, methods for fabricating the microparticles, methods and systems for detecting microparticles, and the methods and systems for using microparticles are described in U.S. Patent Application Publication Nos. 20080038559, 20070148599, and PCT Application No. WO 2007/081410 (all incorporated by reference). Such microparticles are preferably encoded such that the identity of a probe borne by a microparticle can be read from a distinguishable code. The code can be in the form of a tag, which may itself be a probe, such as an oligonucleotide, a detectable label, such as a fluorophore, or embedded in the microparticle, for example, as a bar code. Microparticles bearing different probes have different codes. Microparticles are typically distributed on a support by a sorting process in which a collection of microparticles are placed on the support and the microparticles distributed on the support. The location of the microparticles after distribution on the support can be defined by indentations such as wells or by association to adhesive regions on the support, among other methods. The microparticles may be touching or they may be separated so that individual microparticles are not touching.

The term "sensor" as used herein refers to any device that detects or analyzes an analyte or target in a sample. The sensor includes a recognition element or probe, e.g. enzyme, receptor, molecule, DNA, antibody, or microorganism typically attached to a substrate. A sensor may be associated with an electrochemical, optical, thermal, or acoustic signal transducer that on binding of the probes permits analysis and or detection of chemical properties or quantities of an analyte, or can in combination with a target, result in a signal, detectable by a separate reader. A sensor can be a probe array, such as a microarray with any number of probes attached to a support.

The term "sensor plate" as used herein refers to a plate having one or more sensors, although typically the sensor plate includes a plurality of sensors. The sensor plate can be referred to by a name based on the type of sensor. For example if the sensors on a sensor plate are microarrays, then the plate can be referred to as a probe array plate, or a microarray plate. The sensors can be on the same substrate such that all the sensors can be processed at the same time or the sensors can be separated from each other such that each sensor can be processed separately if desired. In one embodiment, individual sensors or a plurality of sensors on the sensor plate can be separated by a physical barrier resistant to the passage of liquids on a processing plate.

The term "shipping plate" as used herein refers to a device with at least two wells suitable for protecting at least two sensors. The shipping plate is a device used during the handling and shipping of the sensors, such as on a sensor plate. The shipping plate is designed to receive the sensor plate. Once the sensor plate is assembled and inspected, the shipping plate is assembled, contacted, or connected with the sensor plate. Optionally, the shipping plate can have a physical barrier resistant to the passage of liquids and gases around the individual wells or around a plurality of wells. Optionally, the shipping plate may include features to allow multiple sensor plates to be stacked on top of each other.

The term "support" refers to a material or group of materials having a rigid, semi-rigid surface or flexible surface suitable for attaching an array of probes. In one embodiment, the surface may be a combination of materials where at least one layer is flexible. Surfaces on the solid substrate can be of the same material as the substrate. In another embodiment, the substrate may be fabricated form a single material or be fabricated of two or more materials. Thus, the surface may be composed of any of a wide variety of materials, for example, polymers, plastics, resins, polysaccharides, silica or silica-based materials, carbon, metals, inorganic glasses, membranes, or any of the above-listed substrate materials. In a further embodiment, the surface can be supported by a flexible material or a solid material. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. (See, U.S. Pat. No. 5,744,305 for exemplary substrate, which is hereby incorporated by reference herein in its entirety for all purpose).

The term "stain plate" as used herein refers to a device with at least two wells suitable for staining of a sensor plate. In one embodiment, the well depth is optimized to use the minimum volume of sample that is desired. The stain plate is a device used during an assay of the sensor, in particular the staining step for a plurality of sensors, such as on a sensor plate. Taking the sensor plate as an example, the corresponding stain plate is designed to receive the sensor plate. In one embodiment, after the stain solution is deposited into the wells of the stain plate, the sensor plate is assembled with the stain plate such that the active surfaces of the sensors are submerged into the stain solution. Optionally, the stain plate may comprise a physical barrier resistant to the passage of liquids and gases around the individual wells or around a plurality of wells.

The term "wafer" as used herein refers to a substrate having a surface to which a plurality of probes are bound. The substrate can have a flat surface of glass or silica among other materials. Surfaces on the solid substrate can be formed from the same material as the substrate or a different material. Thus, the surface can be any of a wide variety of materials, for example, polymers, plastics, resins, polysaccharides, silica or silica-based materials, carbon, metals, inorganic glasses, membranes, or any of the above-listed substrate materials which may also be present in combinations or layers. In one embodiment, the surface may be optically transparent and may have surface silicon hydroxide functionalities, such as those found on silica surfaces.

The term "wash plate" as used herein refers to a device with at least two wells suitable for washing a sensor. In one embodiment, the well depth and design can be optimized to efficiently wash the sensor with the optimal volume. The wash plate is a device used during an assay of the sensors, in particular the washing step for a plurality of sensors, such as on a sensor plate. Taking the sensor plate as an example, the corresponding wash plate is designed to receive the sensor plate. In one embodiment, after the washing solution is deposited into the wells of the wash plate, the sensor plate is assembled. The active surfaces of the sensors are submerged into the washing solution. Optionally, the wash plate may have a physical barrier resistant to the passage of liquids and gases around the individual wells or around a plurality of wells.

II. SPECIFIC EMBODIMENTS

In one aspect, methods, components and devices for assembling and processing arrays of sensors are provided. These methods and apparatus are particularly useful for packaging sensors for various purposes, for example, transport, shipping, and handling with prevention of damage to the sensors, such as microarrays. The following additionally describes the exemplary design, materials, manufacturing processes and application protocols used for processing and packaging microarrays as an illustration of the various aspect of the invention.

The methods and apparatus are suitable for various types of sensors, such sensors may include nucleic acid sensors such as nucleic acid microarrays. In a preferred embodiment, the sensor may be for instance, a microarray, such as a cDNA array, a peptide array, a bead array or an in situ synthesized high density oligonucleotide array. The microarrays may include a substrate. The term "wafer" as used herein refers to a substrate having a surface to which a plurality of microarrays can be bound. In an embodiment the substrate is a flat surface comprised of glass or silica. Surfaces on the solid substrate may be composed of the same material as the substrate or a different material. Thus, the surface may be composed of any of a wide variety of materials, for example, polymers, plastics, resins, polysaccharides, silica or silica-based materials, carbon, metals, inorganic glasses, membranes, or any of the above-listed substrate materials which may also be present in combinations or layers. In one embodiment, the surface may be optically transparent and may have surface silicon hydroxide functionalities, such as those found on silica surfaces.

For instance, U.S. Patent Pub. 2006/0088863 and U.S. patent application Ser. No. 10/456,370, filed on Jun. 6, 2003 (now abandoned) describe different aspects of constructing sensor plates, sensor strip plates, processing plates or trays, or high-throughput (HT) plates or trays, etc. which may be useful in conjunction with the invention. Each of these applications is hereby incorporated by reference herein in their entirety for all purposes.

Sensor Plates

A microarray plate can also be referred to as a sensor plate or array of sensors. In the exemplary embodiment, the array of sensors or sensor plates allow a plurality of sensors to be processed simultaneously in an assay process of an HT analyzer, such the GENETITAN® instrument (Affymetrix, Inc.). The dimensions of a sensor plate 200 may vary depending on the size and number of the sensors, and the processing methods and apparatus. The HT analyzer, in a preferred aspect, may process the array of sensors with automation of the hybridization, washing, staining and scanning processing of the array of sensors.

According to one embodiment, a sensor plate is assembled by attaching a substrate with a plurality of sensors onto a solid support or a support plate.

In one aspect of the invention, as illustrated in FIGS. 1A, 1B, 1C, 2A, and 2B, a microarray plate 200 is assembled by attaching a wafer section 110 with a plurality of sensors onto a support plate 205.

According to one aspect, the microarray plate 200 includes a wafer section 110 as the substrate. Typically a wafer includes a plurality of synthesized microarrays 101, for example, a wafer may include 16, 49, 64, 81, 100, 144, 169, 196, or 289 microarrays varying according to the size of the wafer and the size of the microarrays synthesized thereon. A wafer 100 can be diced various ways to create wafer sections and wafer strips, for example, a wafer square (e.g. 2×2, 3×3, 4×4, 5×5 microarrays), a wafer strip (e.g. 1×2, 1×3, 1×4, 1×5, 1×6 . . . , 2×3, 2×4, 2×5, 2×6, . . . 3×4, 3×5, 3×6, 3×7 . . . , etc), wafer section such as a rectangle or a combination of the different configurations thereof. FIGS. 1A, 1B, and 1C illustrates an example of how an undiced wafer with 144 microarrays (12×12) can be diced into several diced smaller wafer sections and wafer strips. A wafer section 110 of 8×12 microarrays 110 and four wafer strips 111 of 8 microarrays are formed by dicing on the lines 102 indicated on the undiced wafer in FIG. 1A. The resulting diced wafer section and wafer strips are shown in FIGS. 1B and 1C. In addition, one wafer may have multiple designs, sizes, shapes or formats of probe arrays. For example, wafer 100 shown in FIG. 1A illustrates a wafer with two different sizes of probe arrays. In some aspects the wafer is sized to fit the support plate without dicing. For example, the starting wafer used for probe synthesis may be the size of the sub-wafer 110.

Figure 2B:
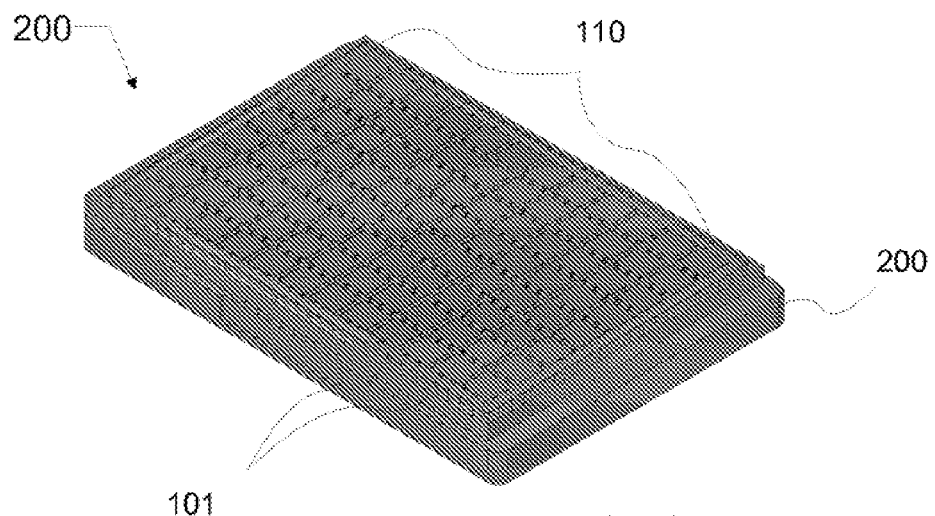

According to another aspect, a support plate 205 is provided, as illustrated in FIG. 2A. A support plate can also be referred to as a solid support. The wafer section 110 is assembled onto the support plate 205 to form the microarray plate 200 as illustrated in FIG. 2B. The wafer section 110 comprises a plurality of microarrays 101 each having a synthesized side with bound polymers 103 and an inactive side 104. The wafer section is assembled directly onto the support plate to produce a microarray plate as shown in FIG. 2B.

The support plate 205 can receive the substrate in a position that is fixed and aligned according to a pre-determined alignment. The pre-determined alignment of the sensors may vary according to the analyzer used to process the sensor plate 200. For example, processing a sensor plate 200 in the GENETITAN® instrument may require a rectangular array of sensors 101, wherein adjacent sensors 101 of the array are separated by approximately 9 mm along the direction of the length and width of the array. The pre-determined alignment and spacing requirements may vary in different HT analyzers. The alignment features of a support plate can include any feature that guides the array of sensors in a pre-determined position. In this example, the wafer is aligned to the support plate with a pre-determined alignment using the edge of the wafer as the alignment features. The wafer is fixedly attached to the support plate forming an array of sensors. The substrate protrudes from the support plate sufficiently to facilitate dipping the substrate into a reservoir of a processing plate.

The support plate 205 may be of any shape or size, so long as the support plate can receive the substrate of the plurality of sensors in a fixed aligned position so they can be processed within an assay protocol. In another embodiment, the support plate 205 is constructed such that a sensor plate 200 assembled using support plate 205 can be processed within an HT analyzer, such as the GENETITAN® instrument, for example. In one embodiment, the support plate 205 is rectangular in shape and includes four side members, such as the support plates shown in FIGS. 2A and 4B. The support plate 205 preferably includes a coupling surface 210, alignment features 211, and structural elements 212 that receive a corresponding surface and alignment features of the substrate. The alignment features 211 of a support plate can include any feature that guides the substrate to a pre-determined position. Examples of an alignment feature include, for example, holes, posts, a raised edge, and an indentation. Structural elements 212 support the substrate of the plurality of sensors to maintain the structure of the substrate. Examples of structural elements include, for example, ridges, walls, and columns.

In general, support plate 205 is constructed from a material that is compatible with the chemical reactants, the operating environment (including temperature) and solvents that are used in the assay process. Any of a variety of organic or inorganic materials or combinations thereof, may be employed for the support plate including but not limited to metals, composites, plastics, such as polypropylene, polystyrene, polyvinyl chloride, poly-carbonate, polysulfone, etc.; nylon; PTFE, ceramic; silicon; (fused) silica, quartz and glass. According to one embodiment, in providing a disposable part, the support plate (205) is made out of a moldable material such as plastic. In circumstances where an assay requires a high hybridization temperature and cold temperature storage, the support plate 205 can be made of any material which can withstand high temperatures for hybridization and be stored in cold temperatures for storage (e.g. cyrolite, Hi-Lo acrylic, polycarbonate, etc.).

Figure 4A:
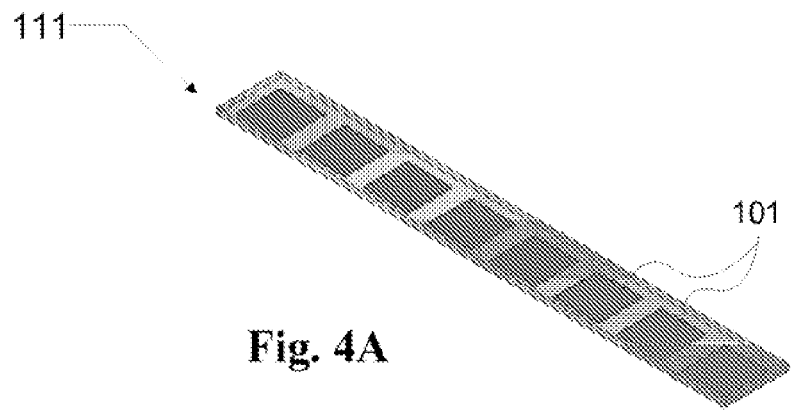
FIGS. 4A, 4B, and 4C depict parts of an exemplary microarray strip plate.
Figure 4B:
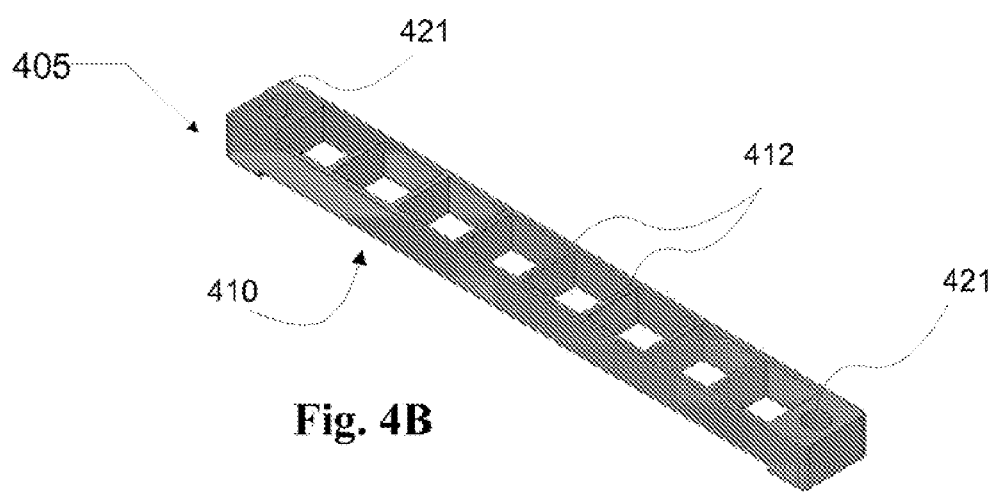

Support plate 205 may be solid, semi-rigid, flexible or a combination thereof and be of any shape, although preferably the support plate is rigid so as to support the substrate comprising the plurality of sensors, such as a wafer section 100 or a wafer strip 111 in a fixed aligned position suitable for an assay process. The dimensions of the support plate should accommodate the size limitations or requirements of a particular sensor analyzer or assay process. The support plate can be formed by machining, molding, mechanical forming, and the like. In one aspect, the dimensions of the processing support plate are about 5 mm to about 400 mm in length, about 10 mm to about 400 mm in width, and about 0.25 mm to about 25 mm in depth. But these dimensions are only general guidelines and may vary depending on the sensor dimensions, a user's needs or other requirements, etc. By way of illustration only, non-limiting examples of different-shaped support plates 205 or support strip plates 405 are shown in FIGS. 2A and 4B.

According to one embodiment, the support plate 205 includes structural elements 212 which ensure that that substrate maintains it structure, for example, the structural elements 212 illustrated in FIG. 2A are ridges or walls that support the back of the wafer such that the wafer remains flat. In this example, the walls contact the perimeter or border surrounding each sensor on the inactive side of the wafer. The ridges assist in maintaining the flatness of each microarray. In one embodiment, the height of the ridges can be about 1 mm to the full depth of the wells, for example, about 2.54 cm.

In an alternative embodiment, the support plate 205 includes a gasket or an elastomeric seal that acts to seal the processing fluids between the sensor plate 200 and a processing plate, for example, to prevent contamination between sensors 101 of a sensor plate 200 during processing. In another embodiment, the support plate includes an attachment feature for attaching the support plate 205 to a processing plate or cover.

According to another embodiment of the invention, the support plate can be solid without ridges; the solid area would support the substrate. In this example, the plate is made of a material that would provide a flat surface, for example, a machined solid stainless steel part.

The wafer can be attached to the support plate by fasteners, bonding, ultrasonic welding, and the like. In one aspect of the invention, a curable adhesive can be used to bond the perimeter of the wafer to the top surface of the perimeter of the support plate such that the ridges are supporting each microarray. The curing process can be performed through the top surface of the wafer, from the side, or a combination thereof to bond the wafer to the support plate.

The support plate can be designed such that various sizes of wafers or wafer sections or wafer strips can be attached. The design of the support plate can also be customized to fit various sizes of the substrates with a plurality of sensors. In some embodiments, the support plate can be made of an optically clear or transparent material such that the transparency characteristic can assist in the manufacturing of the sensor plate.

Moduled Sensor Plate Comprising a Plurality of Sensor Modules

A moduled microarray plate can also be referred to as a moduled sensor plate. In one embodiment, a moduled sensor plate includes a plurality of sensor modules attached to a support frame or a frame. The sensor modules may be placed separately into the frame. There are several ways the sensor modules can be attached to the frame, including but not limited to various attachment mechanisms, for example, holes and pegs. The pegs may be fitted into the holes during the assembly of the sensor strips into the frame to align the sensor strips into a defined orientation within the frame. These attachment mechanisms may include a coupling surface and but can be any type of method that functions to attach one part to another. For example, a plurality of one type of attachment means or a combination of different types of attachment means can be used to attach the sensor modules to the frame. In one embodiment, the sensor modules include at least one support plate module that can be attached to a frame using features which corresponds to at least one attachment feature on the frame. The coupling surface on the sensor module couples with the coupling surface on the frame. In one aspect of the invention, the attachment means may also include an alignment feature on the sensor module to attach the module to the alignment feature on the frame in the pre-determined alignment, as discussed above. In some embodiments, the alignment features can be referred to as attachment features since these features may act as both alignment and attachment features. Alternately, the alignment feature may be a separate feature or mechanism independent of the attachment means. The frame may be constructed in any shape and may include any number of modules so long as the frame can receive a plurality of sensor modules in a fixed aligned position to form a moduled sensor plate suitable for assay processing. The number of sensor modules in a moduled sensor plate will depend on several factors, such as the requirements of the user, the size and number of the sensor, the size of the module, the size of the support structure, etc. A sensor cover may also be used to protect some sensors of the moduled sensor plate from contamination while other sensors on the moduled sensor plate are being processed.

Figure 4C:
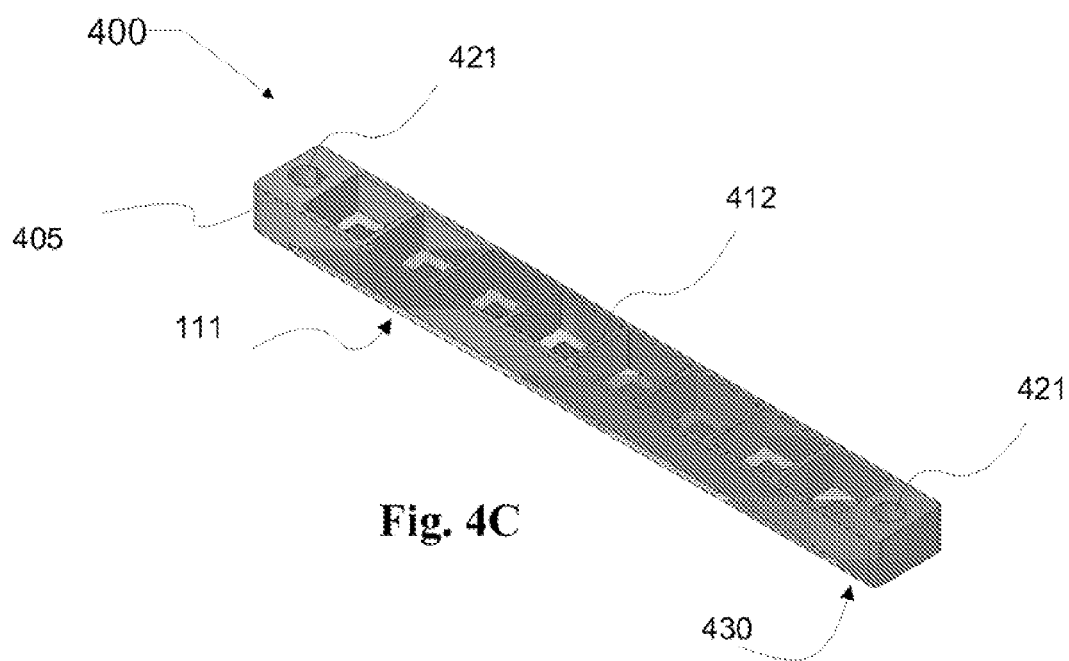
Figure 5A:
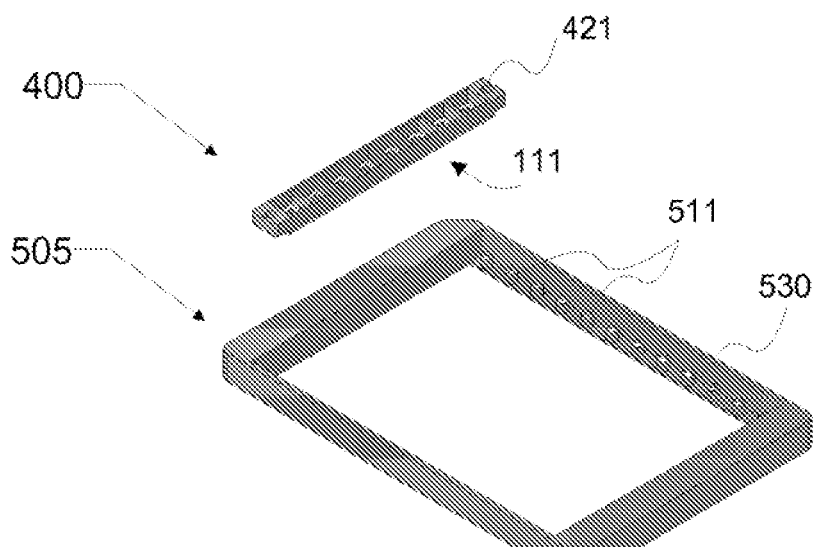
FIGS. 5A, 5B, and 5C depict parts of an exemplary moduled microarray plate.
Figure 5B:
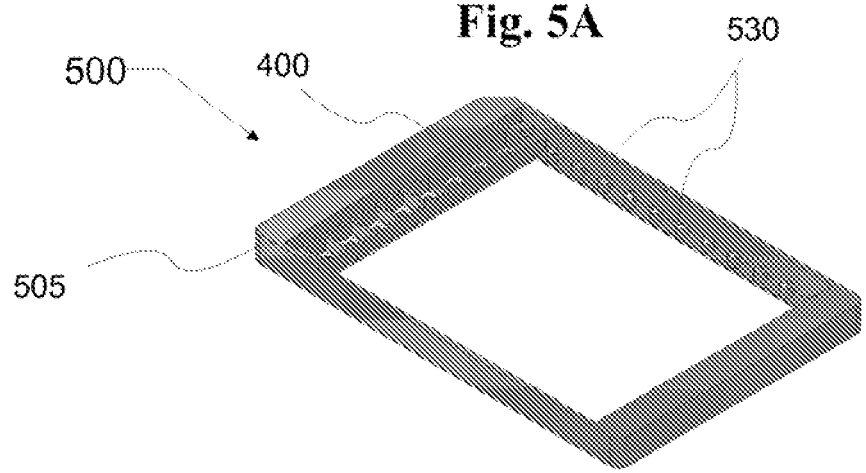
Figure 5C:
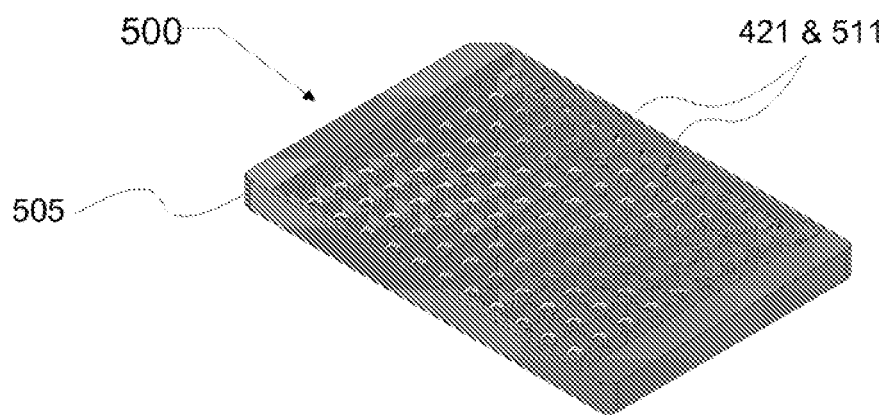

In one embodiment, a microarray plate 200 includes a plurality of microarray strips 400 attached to a frame 505 as shown in FIG. 5C. The microarray strips 400 may be placed separately into the frame 505. The microarray strips 400 are attached to the frame 500 by mating the strip-to-frame alignment features to the frame-to-strip alignment features on the frame 505. In this example, the strip-to-frame alignment features are holes 421 and the frame-to-strip alignment features are pegs 511 as shown in FIGS. 4C and 5A. The pegs 511 are fitted into the holes 421 during the assembly of the microarray strips 400 into the frame 505 to align the microarray strips 400 into a defined orientation within the frame 505. These attachment mechanisms may include a strip-to-frame coupling surface 430 on the microarray strip and a frame-to-strip coupling surface 530 on the frame 505 as illustrated in FIGS. 4C, 5A, and 5B. In one embodiment, the microarray plate includes a plurality of microarray strips that can be attached to a frame 505 using strip-to-frame alignment features 421 which corresponds to at least one frame-to-strip alignment feature 511 on the frame 505. The strip-to-frame coupling surface 430 on the microarray strip couples with the frame-to-strip coupling surface 530 on the frame 530.

In one aspect of the invention, as illustrated in FIGS. 5A, 5B, and 5C, a sensor plate 200 is assembled by attaching a plurality of sensor modules 400 within a frame 505. The frame 505 can receive the plurality of sensor modules in positions that are fixed and aligned according to a pre-determined alignment. The pre-determined alignment of the sensors modules may vary according to the analyzer used to process the sensor plate 200. In many embodiments, the fixed position constrains the movement of the modules 400 in each direction so as to allow full rotational movement of the frame in each direction without dislodging or altering the alignment of the sensor modules 400 relative to the frame 505. Having the modules 400 fixed in a pre-determined alignment relative to the frame allows the sensor modules 400 to be handled, shipped, and processed without altering the position of the sensors 101 relative to the frame 505. This aspect of the invention also facilitates assay processing, which typically requires turning the sensor plate 200 upside down to insert the sensors 101 into the wells of processing plate so that the active side 103 can be contacted with a sample.

In one embodiment, the sensor modules 400 include solid supports 405 having a rectangular base protrusion extending approximately the same distance from one side of the base portion. In this embodiment, the rows of sensors are evenly distributed across the plate.

Sensor Modules

A microarray strip plate can also be referred to as a sensor strip and a sensor module. The sensor modules include at least one sensor and a solid support or strip support 405. In one embodiment, the sensor module may include a sensor which may be disposed on a substrate such as a wafer. The substrate may be attached to a solid support where the sensors are positioned on a protrusion. In one embodiment, the protrusion may be dimensioned or shaped to support the substrate with a plurality of sensors of varying shapes and sizes, for example a rectangular array wafer may be supported by a solid support having a rectangular cross-section. The protrusions may extend from about 1 mm to about 100 mm from the base portion to facilitate placing the sensors 101 within the wells of a processing plate, so as to expose the active side of the sensors to a processing fluid in the bottom of the tray. In certain embodiments, the protrusion extends within a range of 1 mm to 30 mm, for example approximately 2.54 cm.

Figure 3:
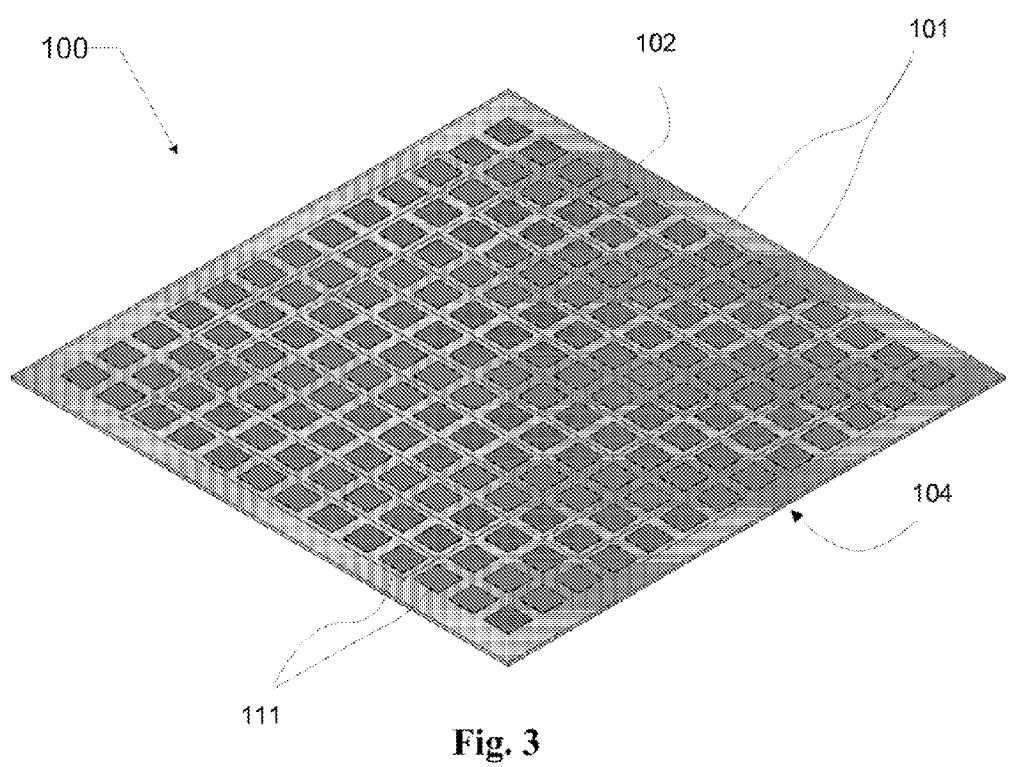
FIG. 3 depicts an example of how a wafer can be diced into a plurality of wafer strips.

As discussed above, an undiced wafer 100 can include any number of microarrays 101 and be of various designs and formats. FIG. 3 illustrates another example of how an undiced wafer with can be diced into several diced wafer sections and wafer strips. In this example, an undiced wafer that includes 169 microarrays (13×13) is outlined 102 to be diced into 18 wafer strips 111 of 1×8 microarrays. A single wafer strip 111 of 1×8 microarrays is shown in FIG. 4A. A microarray strip plate 400 as illustrated in FIG. 4C can be formed by combining a diced wafer strip 111 as shown in FIG. 4A to a strip support 405 as shown in FIG. 4B according to an embodiment. The microarray strip plate comprises a plurality of microarrays aligned in a row.

According to one aspect, a wafer section including a plurality of microarrays is attached to a strip support by an attachment method as shown in FIG. 4C. The attachment method may include but is not limited to fast fasteners, bonding, various adhesives, ultrasonic welding, and the like.

The microarray strip plate 400 include a strip coupling surface 410 for fixedly attaching the wafer strip 111 to the strip support 405 in the fixed aligned position. The strip coupling surface 410 attaches the microarray strip plate 400 by interfacing with a corresponding strip coupling surface 410 of the strip support 405 which includes the surface of the strip structural elements 412.

The microarray strip plate 400 also can include a strip alignment feature 411, which aligns the microarray strip plate 400 according to the pre-determined alignment before or as the strip coupling surface 210 fixedly attaches the wafer strip to the strip support. The strip alignment feature 212 may include a number of different features, including but not limited to, for example, a raised edge, a peg, and a hole.

According to another embodiment, the microarray strip plate 400 also can include a strip-to-frame alignment feature 421, which aligns the microarray strip plate 400 according to the pre-determined alignment before or as the strip to plate coupling surface 430 fixedly attaches the microarray strip plate to the frame 505. The strip to plate alignment features 421 may include a number of different features, including but not limited to, for example, a raised edge, a peg, and a hole.

Frame

The frame may be of any shape or size, so long as the frame can receive the sensor modules in a fixed aligned position so as to be processed within an assay protocol. In many embodiments, the frame is rectangular in shape and includes four side members. The frame may include a frame-to-strip coupling surface 530 and an alignment or attaching feature 511 that receives a corresponding strip-to-frame coupling surface 430 and alignment or attachment feature 421 of a sensor module.

In general, frame is constructed from a material that is compatible with the chemical reactants, the operating environment (including temperature) and solvents that are used in the assay process. Any of a variety of organic or inorganic materials or combinations thereof, may be employed for the frame including but not limited to metals, composites, plastics, such as polypropylene, polystyrene, polyvinyl chloride, poly-carbonate, polysulfone, etc.; nylon; polytetrafluoroethylene (PTFE), ceramic; silicon; (fused) silica, quartz and glass. In circumstances where an assay requires a high hybridization temperature and cold temperature storage, the frame can be made of any material which can withstand high temperatures for hybridization and be stored in cold temperatures for storage (e.g. cyrolite, Hi-Lo acrylic, polycarbonate, etc.).

Frame may be solid, semi-rigid, flexible or a combination thereof and be of any shape, although preferably the frame is rigid so as to support the sensor modules 10 in a fixed aligned position suitable for an assay process. The dimensions of the frame should accommodate the size limitations or requirements of a particular sensor analyzer or assay process. The frame can be formed by machining, molding, mechanical forming, and the like. Preferably, the dimensions of the processing frame are about 5 mm to about 400 mm in length, about 10 mm to about 400 mm in width, and about 0.25 mm to about 25 mm in depth. But these dimensions are only general guidelines and may vary depending on the sensor dimensions, a user's needs or other requirements, etc.

According to one embodiment, a frame 505 is constructed such that a moduled microarray plate 500 can be assembled by attaching a plurality of microarray strip plates 400 onto the frame 500. The moduled microarray plate 500 can be processed within an HT analyzer, such as the GENETITAN® instrument, for example. The frame 505 includes a frame-to-strip coupling surface 530 and an alignment feature 511 that receives a corresponding strip-to-frame coupling surface 430 and alignment feature 421 of a microarray strip as illustrated in FIGS. 5A and 5B.

Processing Plates

Figure 6A:
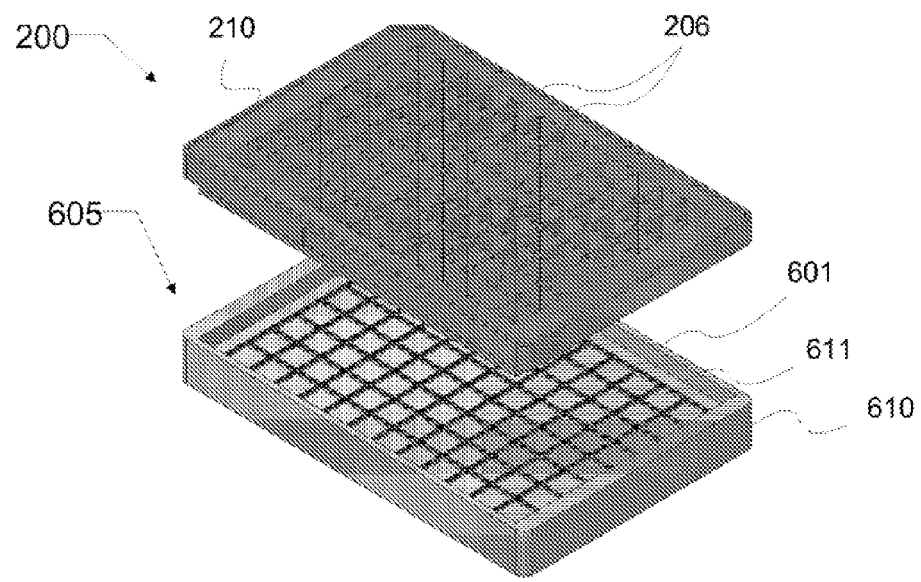
FIGS. 6A and 6B depict an exemplary microarray plate and a hybridization tray.
Figure 14A:
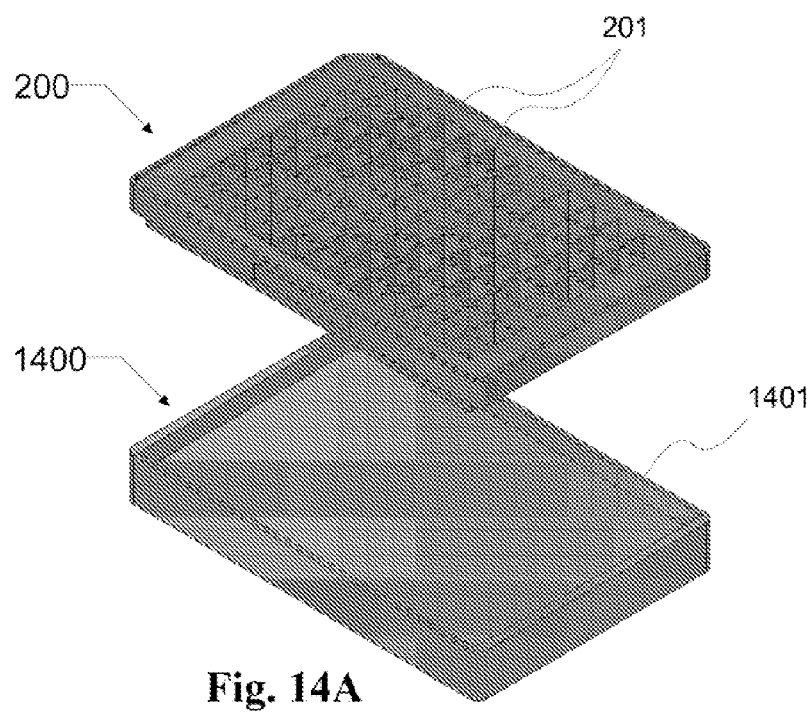
FIGS. 14A and 14B depict an exemplary microarray plate and a stain plate.
Figure 16A:
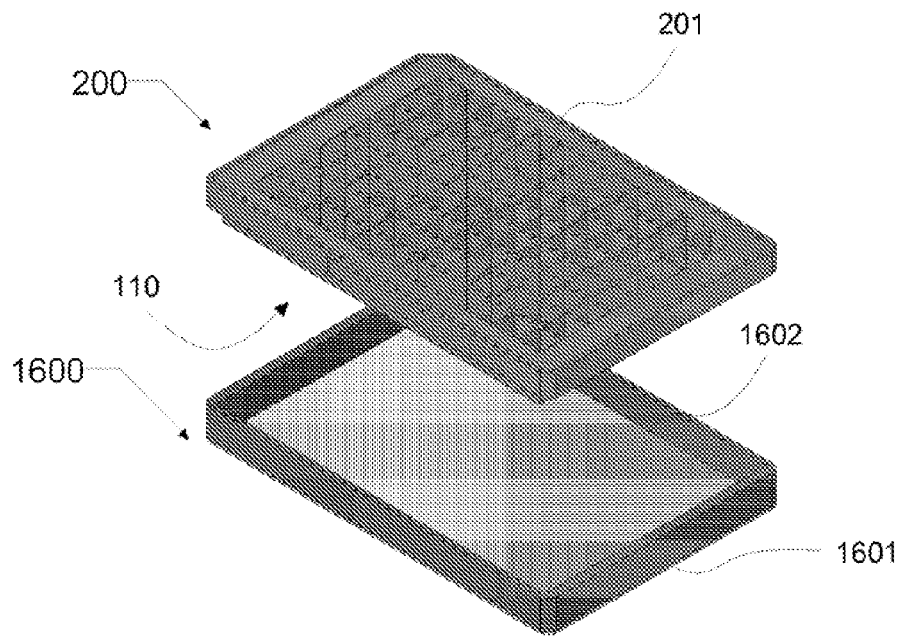
FIGS. 16A and 16B depict an exemplary detection plate.

A processing plate can also be referred to as a processing tray. The term "plate" and "tray" can be used interchangeably. Examples of a processing plate include According to one aspect, the sensor plate attaches or interfaces with a processing plate. Typically, a processing plate includes a plurality of wells, each well corresponding to a sensor of the sensor plate. In many embodiments, each sensor of the sensor plate protrudes outward from a side of the sensor plate on a square peg-like protrusion. In one aspect of the invention, example of a processing plate include a hybridization plate 605, washing plate 1400, stain plate 1400, and detection plate 1600 or other assay plates such as a shipping plate, or a packaging plate all of which are described in detail below. Examples of a hybridization plate 605, washing plate 1400, stain plate 1400, and detection plate 1600 are illustrated in FIGS. 6A, 14A, and 16A. The number of wells in a processing plate can be at least as great as the number of microarrays to be tested on the microarray plate, such as the hybridization plate. In an exemplary embodiment, the processing plate is a rectangular hybridization tray made up of a 12 by 8 matrix of square wells that are open to a receiving side of the hybridization tray. Each square well is dimensioned so that the well receives a sensor of the sensor plate. The openings of the wells may be of any shape such as, for example, rectangular, square, circular, oval, elliptical, rectangular or square with rounded corners. The bottom of the wells may be level, conical, or slanted. The wells are dimensioned so as to use a minimal amount of fluid in each well, while still exposing each sensor to the fluid during an assay process, for instance during the staining, hybridization or detection processes. The dimensions of the opening of the wells are dependent on the dimensions of the microarrays aligned with the well opening. Preferably, the dimensions of the well openings are about 0.5 mm to about 40 mm in length and about 0.5 mm to about 40 mm in width, more preferably, about 1 mm to about 10 mm in length and about 1 mm to about 10 mm in width. Preferably, the volume capacity of the wells is about 100 µl to about 300 µl, more preferably, about 1 µl to about 100 µl. In one embodiment, the processing plate is similar to a standard microtiter plate, which is used for high throughput analysis, such as, for example a 24-, 96-, 256-, 384-864- or 1536-well plate. The hybridization tray may be a standard off-the-shelf model or may be a customized tray. In some embodiments, the tray has four pins, one at each corner of the receiving side that fit into corresponding holes on each corner of a rectangular sensor plate 200 of similar size. The pins act to attach and align the sensor plate 200 to hybridization tray 605 to ensure each sensor 101 is placed within a well of the hybridization tray 605. The tray or sensor plate 200 may also include a gasket that fits around the edges of the tray or plate so as to contain fluid between the plates or between each wells during processing and prevent contamination of the sensors between wells.

In general, a processing plate can be made from any material that is compatible with the chemical reactants, the other operating environment (such as temperature) and solvents that are placed in the wells. Any of a variety of organic or inorganic materials or combinations thereof, may be employed for a processing plate including, for example, metal, plastics, such as polypropylene, polystyrene, polyvinyl chloride, polycarbonate, polysulfone, etc.; nylon; PTFE, ceramic; silicon: (fused) silica, quartz or glass, and the like. A processing plate may be solid, semi-rigid, flexible or a combination thereof and be of any shape. The processing plate is usually the shape of the wafer and can be, for example, rectangular, strip, diamond, square, circular, oval, or any modifications thereof and so forth depending on how the microarrays are configured on the wafer. By way of illustration and not limitation, examples of different shapes of processing plates or processing strip plates are shown in FIGS. 6A, 7, 8B, 9, 11A, 14A, 15A, 16A, and 17A. The dimensions of the processing plate can be sufficient to allow for a desired number of microarrays of a predetermined size to be processed in a processing plate. The processing plate can be formed by machining, molding, mechanical forming, and the like. Preferably, the dimensions of the processing plate are about 5 mm to about 400 mm in length, about 10 mm to about 400 mm in width, and about 0.25 mm to about 25 mm in depth. But these dimensions are only general guidelines and will vary depending on the sensor dimensions, etc.

The processing plate can be made of any material which can withstand high temperatures for hybridization and can be stored in cold temperatures for storage (e.g. cyrolite, Hi-Lo acrylic, etc.). In a further embodiment of the invention, the processing plate includes a sealing surface 601, such as an elastomeric seal, and alignment features 401. In another embodiment, the processing plate includes a clamping feature. In another preferred embodiment, the elastomeric seal is a gasket.

In circumstances where the reaction requires a high hybridization temperature and cold temperature storage, the processing plate can be made of any material which can withstand high temperatures for hybridization and be stored in cold temperatures for storage (e.g. cyrolite, Hi-Lo acrylic, polycarbonate, etc.).

The advantages of having a system, according to an embodiment of the invention, with a microarray plate comprising a wafer and a support plate are: (1) increase in content (e.g., sequences), (2) increased throughput, and (3) a simple packaging process. In utilizing the wafer, the synthesized area can be increased since one would not have to account for area due to dicing or packaging related to packaging individual chips. In addition, the scan time is reduced because auto-focus on every chip is not needed.

Hybridization Plate

Examples of various types of microarray plates and processing plates are depicted in FIGS. 6-11 according to embodiments of the invention. In these examples, the processing plate is a hybridization plate 605. According to one aspect, a microarray plate 200 attaches or interfaces with a hybridization plate 605, as illustrated in FIG. 6A. Typically, a hybridization plate 605 includes a plurality of wells each well corresponding to a microarray of the microarray plate 200. FIGS. 6A and 6B depicts parts where the microarray plate comprises a wafer with 96 microarrays. FIG. 6A shows the microarray plate 200 being assembled onto the hybridization plate 605. FIG. 6B shows the assembled microarray plate with a hybridization plate 600 that includes 96 wells.

In one embodiment of the invention, a hybridization plate is a plate 610 which comprises a plurality of wells 611, a sealing surface 601, and at least one alignment feature 702 along the borders of the plate which assist in the assembling of the array plate with the hybridization plate. A hybridization plate 605 can include a plurality of wells 611, for example, at least 2, 4, 8, 12, 96, 384 wells where the wells may be arranged in a row or a matrix. As depicted in FIG. 6A, in a further embodiment of the invention, a hybridization plate 605 is designed to minimize fluidic volume introduced during hybridization when the microarray plate is assembled with the hybridization plate. The shape of the hybridization plate may be, for example, rectangular, square, diamond, circular, oval, and so forth. The dimensions of the hybridization plate should be such that they are sufficient to allow for a desired number of wells of predetermined size. The wells are formed by machining, mechanical forming, molding, embossing, stamping and the like. Preferably, the dimensions of the hybridization plate are about 2.54 cm (1") to about 12.7 cm (5") in length, about 2.54 cm (1") to about 8.89 cm (3.5") in width, and about 0.63 cm (0.25") to about 1.27 cm (0.5") in depth. The dimensions will vary depending on the size of the microarray plate.

The hybridization plate can be made from any material that is compatible with the chemical reactants and solvents that are placed in the wells and can sustain high temperatures such as a high temperature molded plastic material (e.g. polycarbonate, polypropylene, etc.). In a preferred embodiment of the invention, the hybridization plate is made out of Lexan HPI which is chemically resistant and allows the hybridization plate to withstand high temperatures for hybridization, and cold temperatures for storage. This material enables hybridization conditions at temperatures in excess of 60° C. In a further embodiment of the invention, the hybridization plate is suitable for chemiluminescence.

Figure 6B:
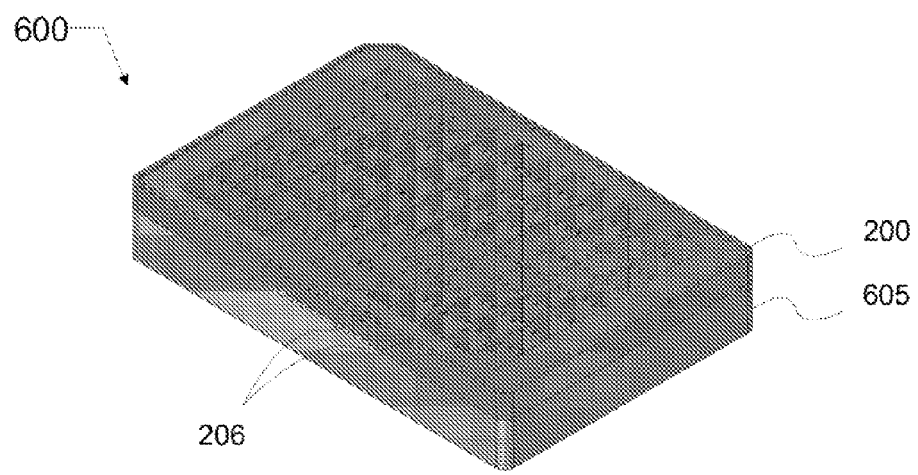
Figure 7:
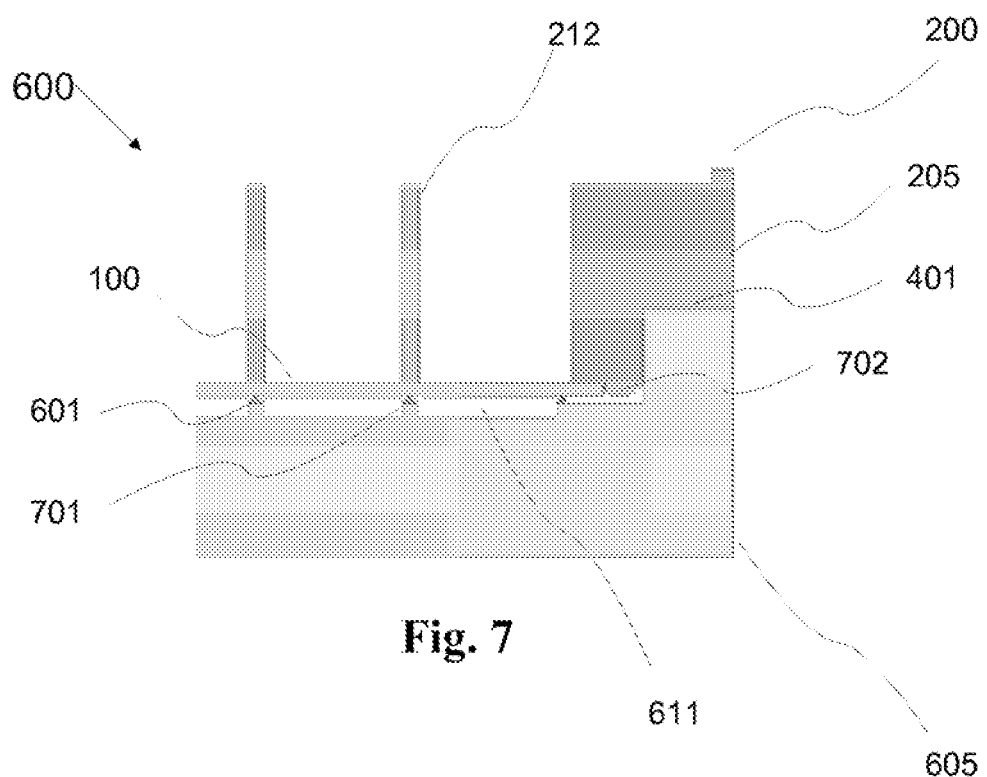
FIG. 7 depicts a cross section view of an assembled exemplary microarray plate with an exemplary hybridization tray.

It is desirable to have a seal between the perimeter of the surface of each microarray and each well to avoid cross contamination between arrays of sensor. Various approaches may be employed. According to one aspect of the invention, a flexible member 601 can be utilized to form the seal as depicted in FIGS. 6B and 7. Preferably, the flexible member is a gasket and the cross sectional shape of the gasket may be, for example, rectangular, or square with straight sides and a flat, concave or convex bottom, and the like. The flexible member maybe, for example, made of elastomer, rubber, flexible plastic, flexible resins, and the like and combinations thereof. The flexible material should be substantially inert with respect to the liquid samples in the wells. Preferably, the dimensions of the gasket are 0.25 mm to about 5 mm deep and about 0.25 mm to 5 mm wide, more preferably, about 3 mm deep and about 3 mm wide. There are several ways to form a seal with a gasket between the microarray plate and the hybridization plate such that the sample does not evaporate and mix between the wells. The gasket can be part of the microarray plate, the hybridization plate or a separate piece like a clam shell device.

FIG. 7 illustrates a cross section of an assembled microarray plate with a hybridization plate 600. The support plate 205 has a top and bottom side. The top side of the support plate includes a plurality of structural elements 412, at least one wafer alignment feature 702 to align the wafer, and at least one frame-to-support plate alignment or attaching feature to align the support plate 205 to a hybridization plate 605. The alignment feature on the microarray plate would align with the corresponding alignment feature on the hybridization plate, such as edge configuration 401 as shown in FIG. 7. The hybridization plate is used to process the microarrays on the wafer 100. The wafer is aligned onto the support plate with the at least one wafer alignment feature 702 on the support plate to produce an aligned wafer. The aligned wafer is attached to the top side of the support plate such that the structural elements 212 support the inactive side of each microarray on the wafer to produce a microarray plate.

In one aspect of the invention, the gasket can be formed around each well as shown in FIG. 7. The design of the wells of the hybridization combined with the design of the microarray plate assists in reducing hybridization target volumes thus minimizing cost for processing the microarray plates. The sealing surface is on top of the walls 701 that make up the wells 611. A hermetic seal necessary for high temperature incubation is created between each microarray 101 and each hybridization well 611 when the hybridization plate and a microarray plate are assembled for the hybridization process. The gasket on the hybridization plate, when assembled with a microarray plate, surrounds the perimeter of each microarray on the microarray plate. The placement, shape, dimensions, or design of the flexible member can be dependent on the dimensions of the hybridization plate, operating temperature and vapor pressure of the liquid sample contained in the wells and so forth. The gasket may also be formed on the hybridization plate by any standard technique such as, for example, over molding, bonding with a pre-formed part, machining and the like. In a preferred embodiment, the hybridization plate includes a gasket that is made of any material known in the art such as a Thermal Plastic Elastomer (TPE) over-mold seal and the like. The sealing surface 301 can be made of any material known in the art such as an elastomeric over-mold seal.

Figure 8A:
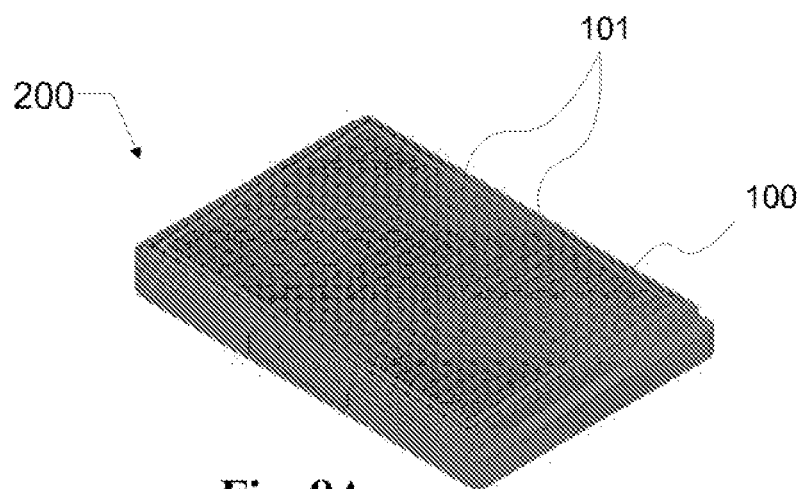
FIGS. 8A, 8B, and 8C depict a further example of a microarray plate and a hybridization plate.
Figure 8B:
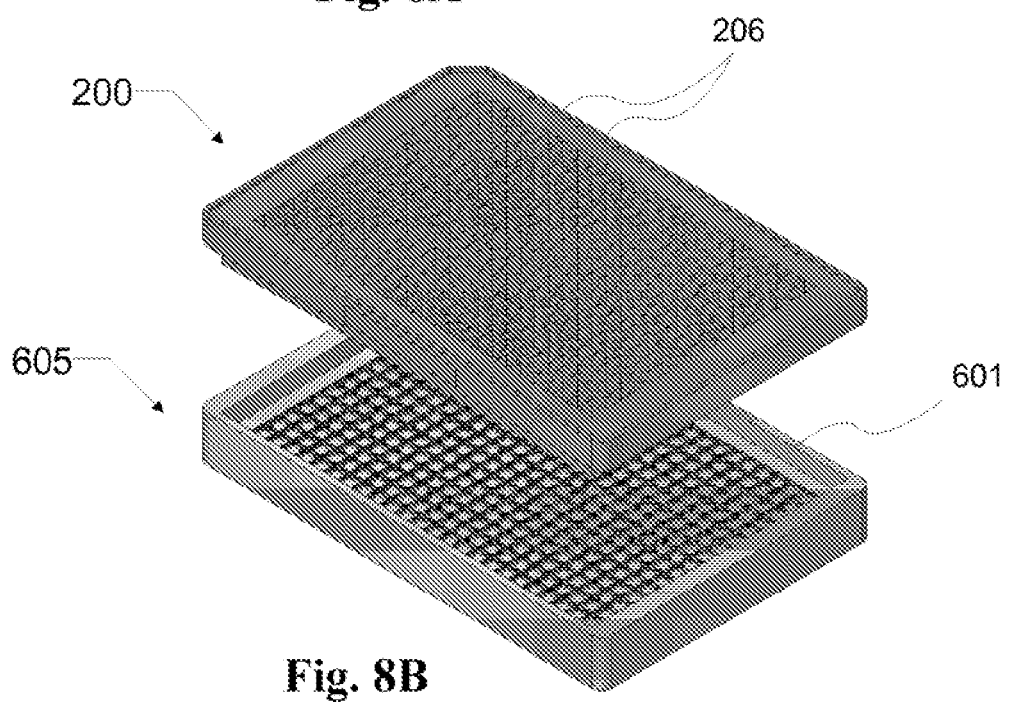
Figure 8C:
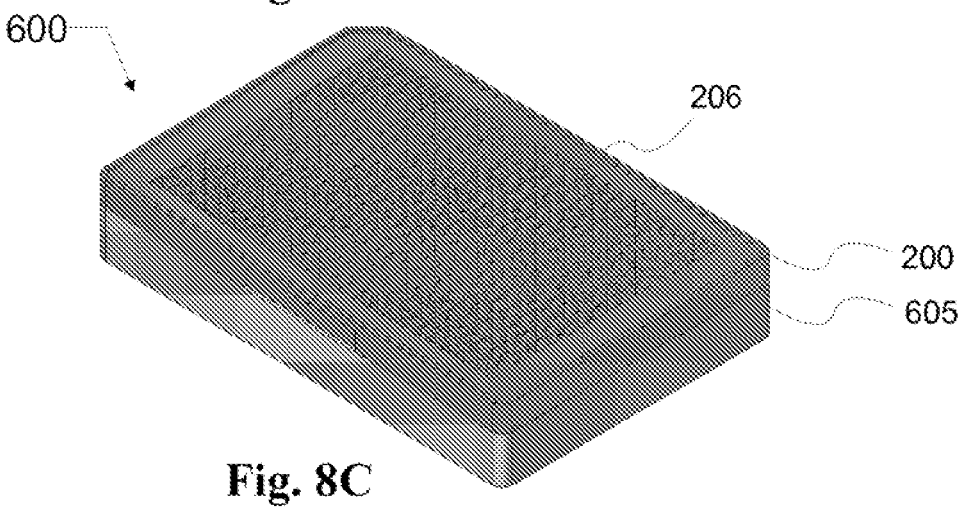

As discussed previously, the wafer can include a number of microarrays. FIG. 8 depicts an example where a microarray plate 200 and hybridization plate 605 includes 384 microarrays according to another embodiment of the invention. FIG. 8A shows the microarray plate 200. FIG. 8B shows the microarray plate 200 being assembled onto a hybridization plate 605 that includes 384 wells. FIG. 8C shows the assembled microarray plate with the hybridization plate 600.

Figure 9:
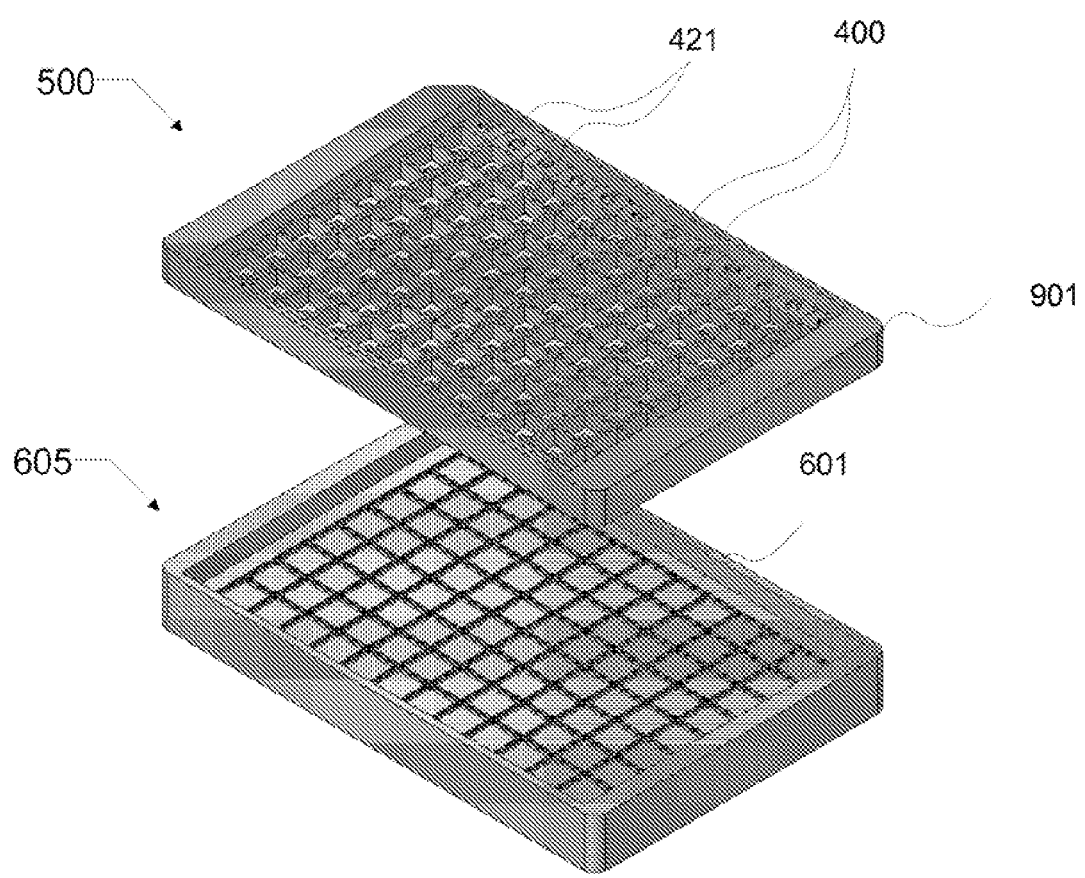
FIG. 9 depicts an example of a moduled microarray plate and a processing plate, where the microarray plate includes 12 microarray strip plates.

Another variation of a microarray plate is shown in FIG. 9, where the microarray plate is a moduled microarray plate comprising of 12 microarray strip plates 400, each comprising 8 microarrays. FIG. 9 shows the moduled microarray plate 500 being assembled onto the hybridization plate 605 with 96 wells.

Figure 10:
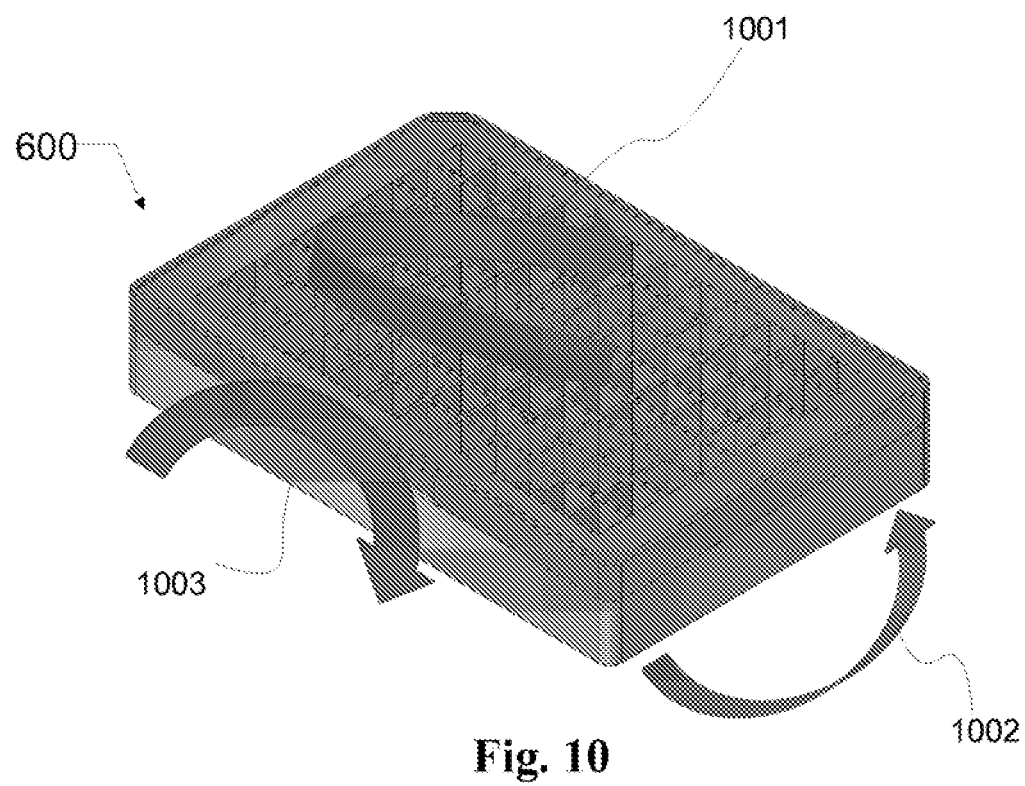
FIG. 10 depicts examples of the various directions that an assembled microarray plate with a hybridization plate can be rotated.

FIG. 10 depicts examples of the various directions that the assembled microarray plate with a hybridization plate can be rotated according to an embodiment of the invention. Hybridization can occur dynamically by rotating the assembled microarray plate with the hybridization plate along one or more axis, for example, circular 1001, up and down 1002, and flipping it over 1003, as shown in FIG. 10. The gap between the bottom of the hybridization well and the surface of the microarray would be large enough to overcome surface tension and allow for liquid movement.

Figure 11A:
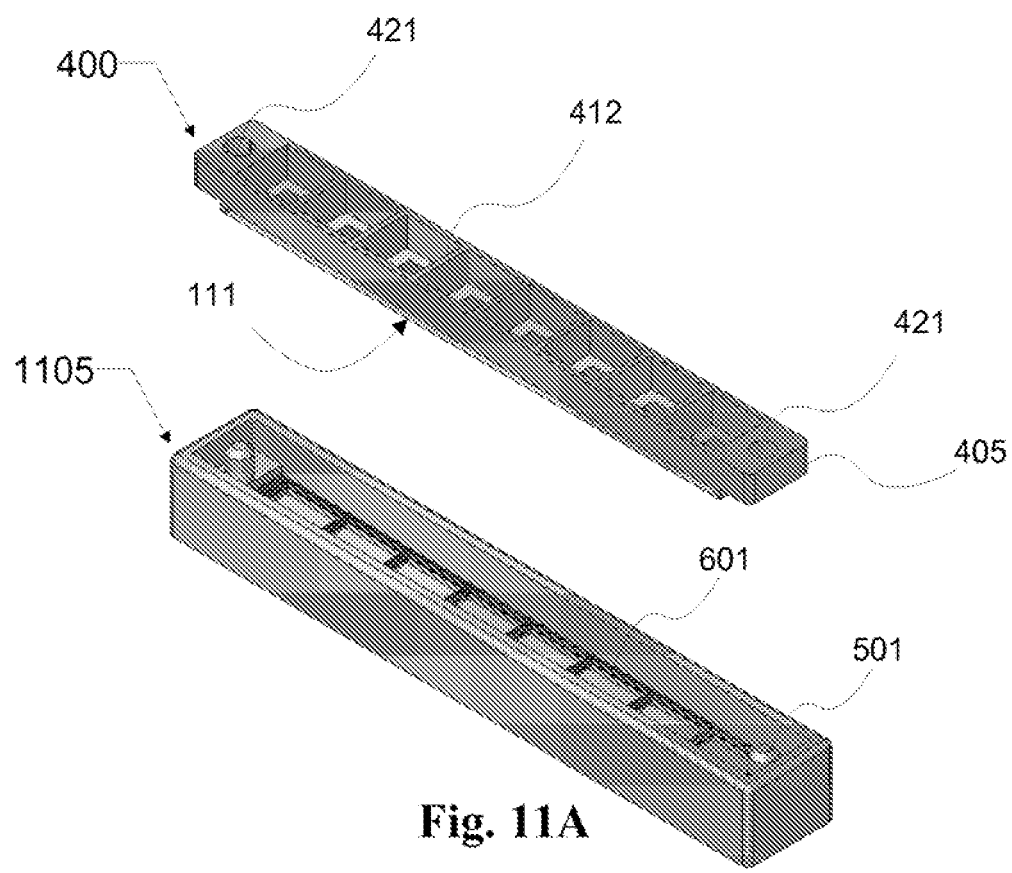
FIGS. 11A and 11B depict an exemplary microarray strip plate and a hybridization strip plate.
Figure 11B:
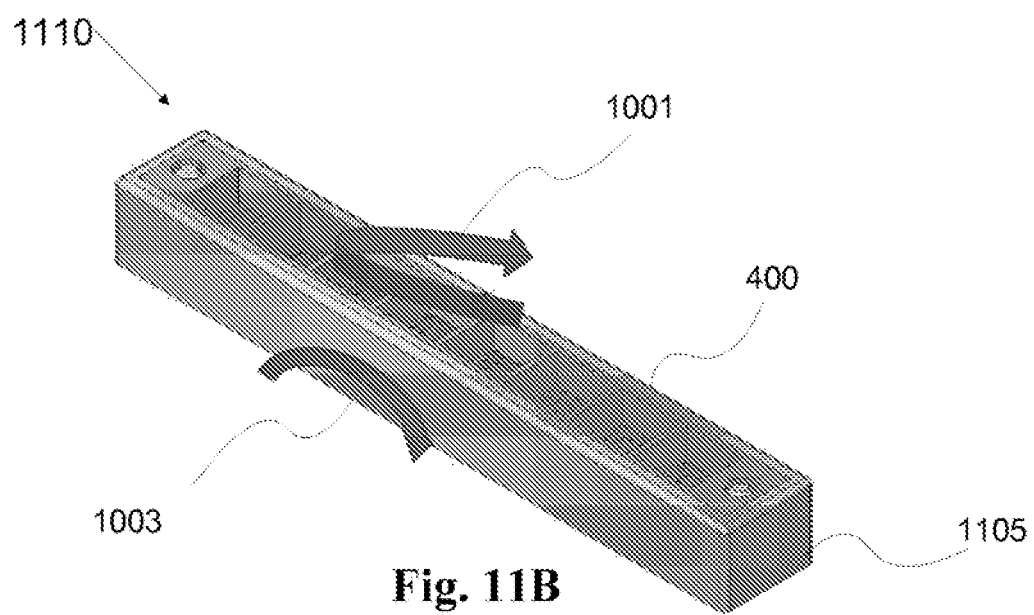

FIGS. 11A and 11B depict a microarray strip plate 400 with a hybridization strip plate 1105 according to an embodiment of the invention. FIG. 11A shows a microarray strip plate 400 being assembled with a hybridization strip plate 1105. FIG. 11B shows examples of directions that an assembled microarray strip plate with a hybridization strip plate 1110 can be rotated, for example, in a circular motion 1001 and flipping it over 1003.

Clamping Device

Figures 12A, 12B:
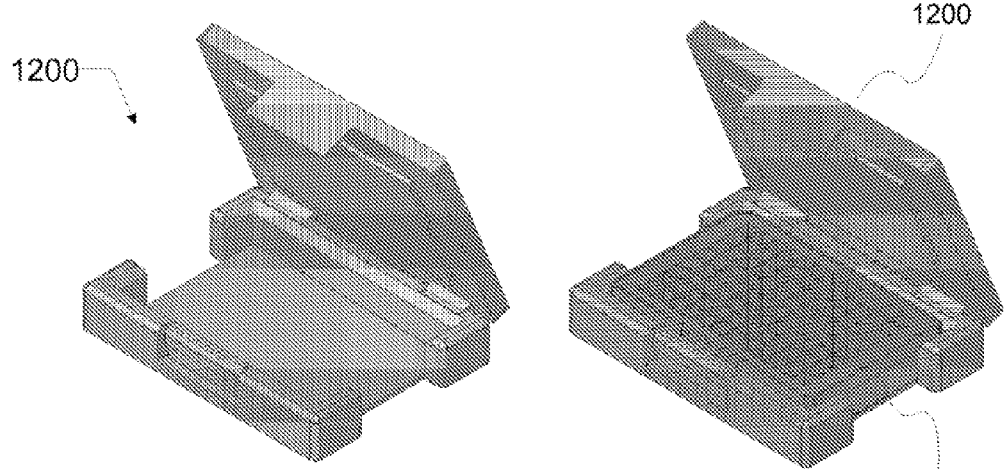
FIGS. 12A, 12B, and 12C depict an exemplary clamping device.
Figure 12C:
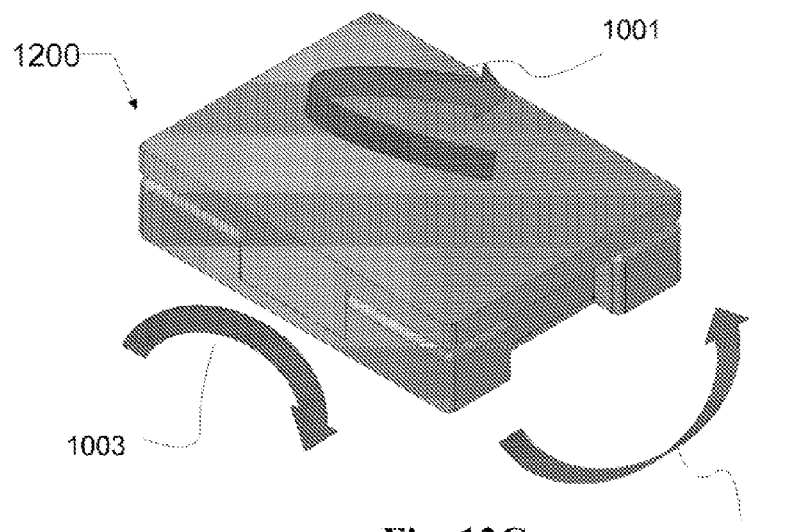

In one embodiment of the invention, the assembly and removal of an assembled microarray plate with a hybridization plate 600 may be performed with a mechanical device such as a clamping device 1200. FIG. 12A shows an opened empty clamping device according to an embodiment of the invention. A microarray plate can be assembled with a hybridization plate and placed into a clamping device as shown in FIG. 12B. The clamping device presses the assembled parts together to form a hermetic seal using the gasket on the hybridization plate. The closed clamping device can be placed into an oven to be rotated in the various directions (for example, upside down, up and down, side to side, clock-wise, counter clockwise etc.) as shown in FIG. 12C.

FIGS. 13A to 13C depict a clamping device according to another embodiment of the invention, where pluralities of assembled microarray strip plates with hybridization strip plates are placed into a clamping device. FIG. 13A shows an opened empty clamping device. FIG. 13B shows a clamping device with a plurality of assembled microarray strip plates with hybridization strip plates. FIG. 13C shows examples of the various directions that the assembled microarray strip plates with hybridization strip plates can be rotated. In an embodiment of the invention, the clamping device 1200 can be machined out of, for example, metal such as stainless steel.

Wash or Stain Plate

Figure 14B:
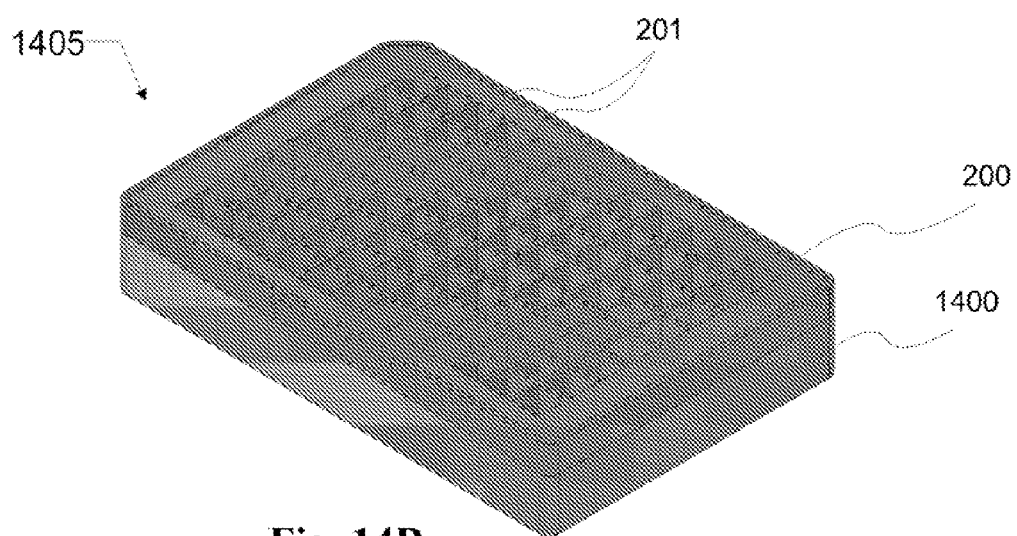

FIGS. 14A and 14B illustrate an exemplary stain or wash plate 1400, which can be used for staining or washing the microarray plate 210 during the staining process or washing process according to an embodiment of the invention. The stain or wash plate 1400 is a plate with no wells but instead these plates have walls 1401 designed to receive the microarray plate. FIG. 14B depicts an assembled array plate with a stain or wash plate 1405. The staining or washing plate is optimized for depth to use the minimum volume of sample desired. The staining or wash plate can include a plurality of wells.

Figure 15A:
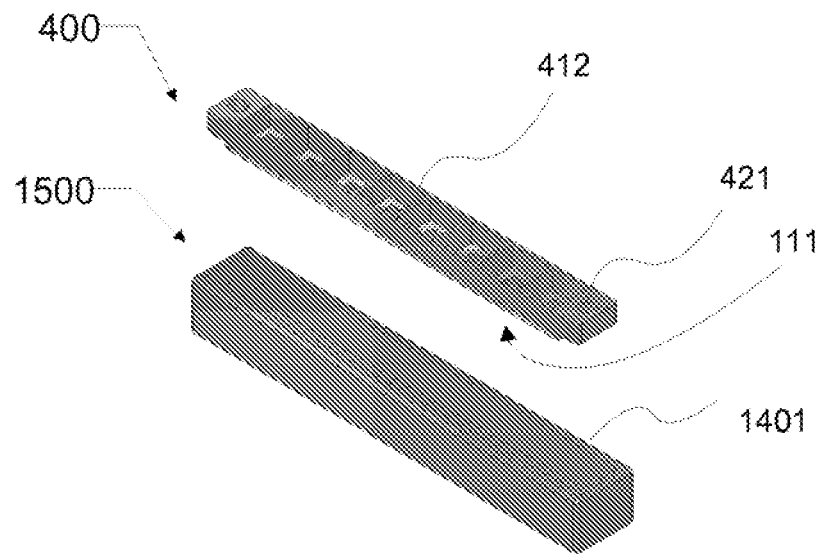
FIGS. 15A and 15B depict an exemplary microarray strip plate and a stain strip plate.
Figure 15B:
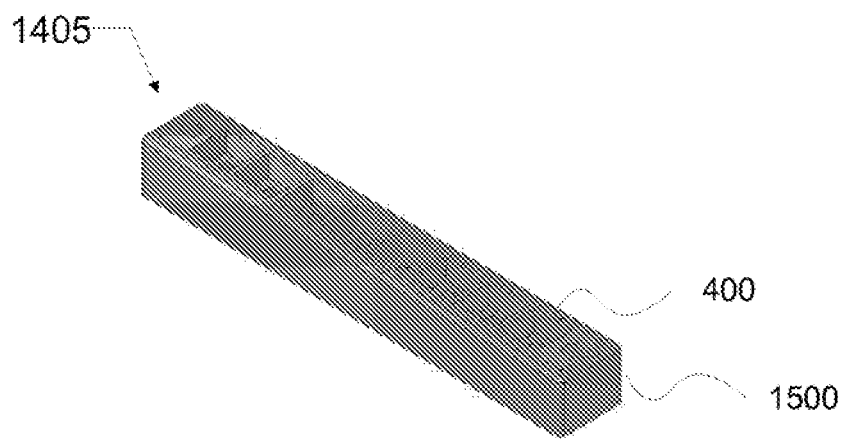

FIGS. 15A and 15B depict a stain or wash strip plate 1500 according to an embodiment of the invention. FIG. 15A shows a microarray strip plate 400 being assembled with a stain or wash strip plate 1500. FIG. 15B shows an assembled microarray strip plate with a stain/wash strip plate 1505.

Detection Plate

Figure 16B:
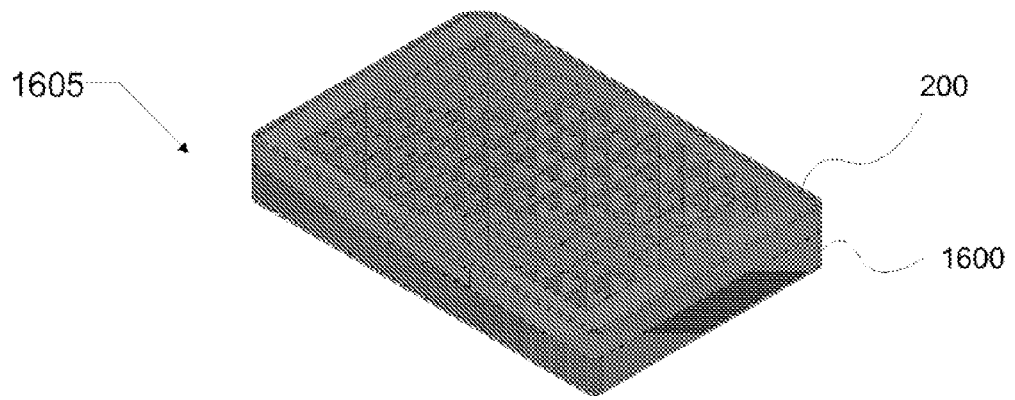

FIGS. 16A and 16B depict an exemplary detection plate according to an embodiment of the invention. A detection plate can also be referred to as a scan plate. FIG. 16A shows a microarray plate 200 being assembled with a detection plate 1600. The detection plate 1600, which is used for processing the microarray plate 200 during the scanning process, comprises a support plate 1601 that is hollow in the middle and a transparent bottom piece 1602 that is designed to receive the microarray plate. FIG. 16B shows an assembled microarray plate with a detection plate 1605.

Figure 17A:
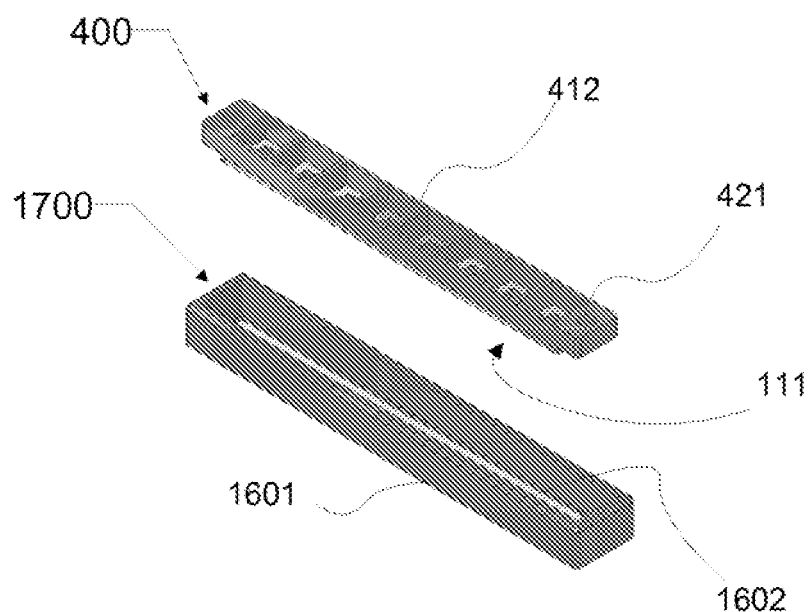
FIGS. 17A and 17B depict an exemplary microarray plate and a scan strip plate.
Figure 17B:
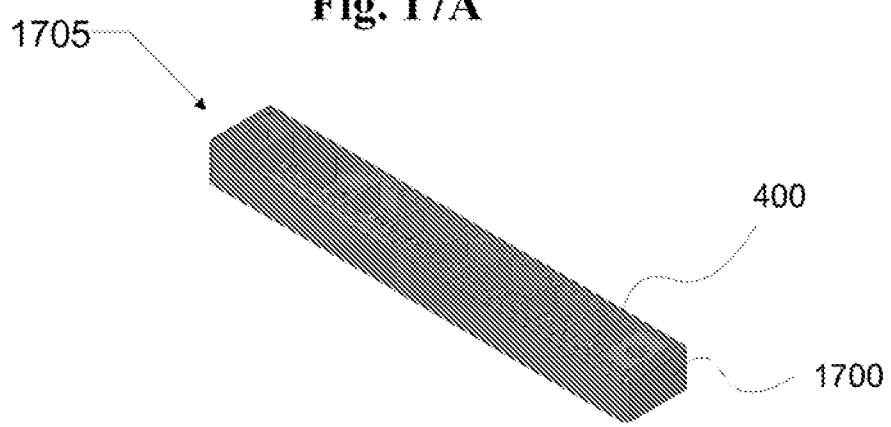

FIGS. 17A and 17B depict a detection strip plate 1700 according to another embodiment of the invention. FIG. 17A shows a microarray strip plate 400 being assembled with a detection strip plate 1700. FIG. 17B shows an assembled microarray plate with a detection plate 1705.

The support plate can be made from any material that is compatible with solvents that are placed in the plate. Any of a variety of organic or inorganic materials or combinations thereof, may be employed for a support plate including, for example, metal, plastics, etc. The optically clear piece must be transparent and distortion free for purposes of imaging the surface of the microarrays. In an embodiment of the invention, the transparent bottom piece can be made from an optically clear and low-fluorescence material 603 such as fused silica, zeonor (zionex), etc. It may be desirable that this material is non-fluorescent in order to minimize the background signal level and allow detection of low level signals from low intensity features of the probe array. The optically clear substrate can be attached to the support plate by using an adhesive, or any other known attachment means. Preferably, the dimension of the gap from the surface of the sensor to the optically clear window is between 100 microns to 2,000 microns, more preferably about 600 microns. A multi-plastic molded design can be used to produce the hybridization and detection plates at very low cost. In addition the design can allow for flexibility to change the thickness of the optically clear window piece to enhance image resolution of the microarray. In one embodiment, the material of the support plate 1601 of the detection plate 1600 can be black or a dark color to minimize reflection during scanning and the optically clear window is made out of fused silica. The microarrays on the wafer can be imaged and scanned using an array plate scanning instrument through the optically clear piece of the detection plate.

Assay Protocol

The arrays and the liquid samples in the wells are maintained in contact for a period of time sufficient for the desired chemical reaction to occur. The conditions for a reaction, such as, for example, period of time of contact, temperature, pH, salt concentration and so forth, are dependent on the nature of the chemical reaction, the nature of the chemical reactants including the liquid samples, and the like. The conditions for binding of members of specific binding pairs are generally well known.

The concept of using separate processing plates for hybridization (and high temperature washing) and scanning enables higher efficiency washes and cleaner images when executing the protocol. In one embodiment of the invention, all three components in the kit (a hybridization plate, a washing plate, staining plate and a detection plate) are disposable so durability and cleanliness is not a requirement beyond a single use. However, since the critical process steps are performed in separate wells, contamination during sequential steps is minimized or eliminated. In addition, the transfer of the microarray plates between steps should facilitate more efficient cleaning of the arrays.

The hybridization and high temperature washes are performed in the wells of these processing plates which are designed to be assembled with the microarray plates.

Normal washing that does not require high temperature incubation, since wash plates will work at a maximum temperature of 70° C., can be performed in standard deep plates which are also very economical in price since they are commercially available. Following hybridization and any other steps requiring rinsing or washing, the microarray plates can be placed into these deep plates for cleaning. Since the wash fluid volume is large, the cleaning process is more efficient and fewer wash steps would be required, thus saving further process time.

In one aspect of the invention, the microarray plate is placed into the processing plate (for example, the hybridization plate, washing plate, staining plate, detection plate, reagent plate or packaging plate) and the processing plate is filled with the desired liquid to contact the microarrays on the wafer. When the microarray plate has completed the hybridization, labeling and washing steps, the microarray plate can be assembled into the detection plate with clean buffer for scanning. The details of the assay are described further in U.S. Patent Publication No. 2006/0088863, which is hereby incorporated by reference herein in its entirety for all purposes.

It would also be understood by any person skilled in the art that there are no limitations as to the size of the wafer attached to the support plate of the current invention.

In the invention, a hybridization volume, for example for a 6.3 mm by 6.3 mm embodiment of a sensor 101, can be designed to be about 12 μl. However, there are no design constraints that would prevent a smaller volume or larger volumes. It would also be understood by a person skilled in the art, that the detection plate described in the invention is not volume sensitive. In the invention, buffer is used as a coupling fluid between the sensors and the bottom of the detection plate, and its total volume is incidental. However, the distance from sensors to the outside surface of the detection plate may need to be kept very small if the scanner objective lens has a short focal length.

It is further understood by any person skilled in the art, that the transparent piece of the detection plate of the present application may have a low fluorescence background. In one example, a scanner with no detection plates has a background of 7 counts, which is a unit of measure of the background noise. The detection plate may have, for instance, a total fluorescence background of 14 counts. The dynamic range of the scanner maybe about 65,000 counts.

According to one aspect of the invention, a method is provided for constructing a microarray plate, wherein a wafer is submerged into a liquid. The wafer has a plurality of microarrays synthesized on one side. A support plate with a plurality of structural elements is provided. The structural elements maintain the flatness of each microarray by supporting the inactive side of each microarray of the assembled microarray plate. The support plate includes at least one support plate alignment feature to align the support plate to a processing plate, wherein the processing plate is used to process the plurality of microarrays on the wafer. The wafer is placed and aligned on top of the support plate by using at least one wafer alignment feature on the support plate. The wafer is directly attached to the top side of the support plate such that the plurality of structural elements supports the inactive side of each microarray on the wafer to produce a microarray plate. In a preferred embodiment, the wafer is diced to a smaller wafer. The wafer can be bonded using a curable adhesive. The adhesive can be cured with a solid state narrow wavelength light source such as an LED, having a wavelength that is from 430 nm to 480 nm. In a preferred embodiment, the wavelength is approximately 455 nm.

In another aspect of the invention, the microarray plate is a microarray strip plate. The microarray strip plate is a plurality of microarray strip plates, wherein each microarray strip plate comprises at least one strip plate to frame attachment feature. The method further comprises a frame. The frame includes a plurality of frame-to-strip plate attaching features. The plurality of microarrays strip plates are attached to the frame by matching the at least one strip plate to frame attachment feature on each microarray strip plate to the plurality of frame-to-strip plate attaching features on the frame to produce a microarray plate.

In another embodiment, the processing plate comprises a sealing surface, such that the sealing surface supports the synthesized side of each microarray on the wafer.

It is to be understood that the description in this application is and not restrictive. Many variations of the invention will be apparent to those of skill in the art upon reviewing the above description. Various alternatives, modifications and equivalents are possible. The description and figures are by way of illustration and not limitation. One of skill in the art would appreciate that the invention is not limited to the specific examples provided. In one embodiment of the invention, the system for processing microarray plates includes various packages such as a microarray plate and a microarray strip plate. The attached drawings illustrate some of the embodiments of these various microarray assemblies. All cited references, including patent and non-patent literature, are incorporated herewith by reference in their entireties for all purposes.

What is claimed is:

1. A probe array plate comprising:
   a wafer having a plurality of probe arrays bound to an active side of the wafer, each probe array surrounded by a border region on the wafer that does not comprise any probe arrays; and
   a support plate comprising structural elements;
   wherein the support plate is fixedly attached to the wafer at an inactive side of the wafer opposite the active side, with the structural elements of the support plate contacting the inactive side of the wafer at positions opposite the border regions surrounding each one of the probe arrays, and wherein the attached wafer protrudes from the support plate.

2. The probe array plate according to claim 1, further including a processing plate contacting the support plate.

3. The probe array plate according to claim 1, wherein each probe array is a microarray and the probe array plate is a microarray plate.

4. The probe array plate according to claim 3, wherein the microarray plate is a microarray strip plate.

5. The probe array plate according to claim 1, wherein the support plate structural elements are ridges or walls.

6. The probe array plate according to claim 1, wherein the support plate further comprises at least one alignment feature that guides the alignment of the wafer with the support plate during manufacturing.

7. The probe array plate according to claim 6, wherein the alignment feature is selected from the group consisting of a hole, a post, a raised edge, and an indentation.

8. The probe array plate according to claim 2, wherein the support plate further comprises at least one alignment feature that aligns the support plate with the processing plate.

9. A moduled probe array plate comprising:
- a plurality of probe array plates according to claim 1, wherein each support plate further comprises at least one attachment feature; and
- a frame comprising a plurality of corresponding attachment features;
- wherein the plurality of probe array plates attach to the frame by engaging the at least one attachment feature on each support plate to a corresponding attachment feature on the frame.

10. The moduled probe array plate according to claim 9, wherein each probe array plate is a microarray strip plate.

11. A probe array plate assembly comprising:
- at least one probe array plate according to claim 1; and
- a processing plate,
- wherein the processing plate is configured to allow insertion of the at least one probe array plate into the processing plate.

12. The probe array plate assembly of claim 11, wherein the processing plate includes a sealing surface that supports the border surrounding each probe array on the active side of the wafer.

13. The probe array plate assembly of claim 11, wherein the processing plate includes a clamping feature.

14. A probe array plate assembly comprising:
- a moduled probe array plate according to claim 9; and
- a processing plate,
- wherein the processing plate is configured to allow insertion of the moduled probe array plate into the processing plate.

15. The probe array plate assembly of claim 14, wherein the processing plate includes a sealing surface that supports the border surrounding each probe array on the active side of each wafer.

16. The probe array plate assembly of claim 14, wherein the processing plate includes a clamping feature.

* * * * *